(12) United States Patent
Ferlic et al.

(10) Patent No.: US 9,561,298 B2
(45) Date of Patent: *Feb. 7, 2017

(54) UNIVERSAL STERILIZING TOOL

(76) Inventors: Michael J. Ferlic, Roseville, MN (US);
Mason J. Ferlic, Roseville, MN (US);
Nicholas R. Powley, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/592,008

(22) Filed: Aug. 22, 2012

(65) Prior Publication Data

US 2012/0315201 A1 Dec. 13, 2012

Related U.S. Application Data

(63) Continuation of application No. 12/300,717, filed as application No. PCT/US2008/076864 on Sep. 18, 2008, now Pat. No. 8,273,303.

(60) Provisional application No. 61/050,769, filed on May 6, 2008.

(51) Int. Cl.
*A61L 2/00* (2006.01)
*A61L 2/26* (2006.01)
*A61L 2/238* (2006.01)
*A61M 39/16* (2006.01)

(52) U.S. Cl.
CPC .............. *A61L 2/26* (2013.01); *A61L 2/238* (2013.01); *A61M 39/16* (2013.01); *A61L 2202/17* (2013.01); *A61L 2202/24* (2013.01)

(58) Field of Classification Search
CPC . A61L 2/235; A61M 39/20; A61M 2005/3106
USPC .......................................... 422/294; 604/905
See application file for complete search history.

(56) References Cited

U.S. PATENT DOCUMENTS

| 1,374,851 | A | 4/1921 | Hirth |
| 2,030,911 | A | 2/1936 | Borden |
| 3,557,989 | A | 1/1971 | Balda |
| 3,661,666 | A | 5/1972 | Foster et al. |
| 3,976,311 | A | 8/1976 | Spendlove |
| 3,987,930 | A | 10/1976 | Fuson |

(Continued)

FOREIGN PATENT DOCUMENTS

| EP | 0227219 B1 | 12/1990 |
| EP | 2606930 A1 | 6/2013 |

(Continued)

OTHER PUBLICATIONS

International Search Report and Written Opinion of international application No. PCT/US2008/076864, mailed Nov. 17, 2008, 18 pp.

(Continued)

*Primary Examiner* — Kevin Joyner
(74) *Attorney, Agent, or Firm* — Faegre Baker Daniels LLP

(57) ABSTRACT

A contoured sterilizing element is configured to conform to the outer and inner surfaces of a working end-site of a medical device such as a catheter hub, luer connector, luer component, needleless access site, and/or access port. The sterilizing element is made from absorbent material and can be pre-moistened or impregnated with an anti-pathogenic agent. The sterilizing element can be contained within a housing that is easily gripped and opened in one hand by the user. The sterilizing element is configured to wipe debris from and to sterilize and/or dry a working end-site of medical device, using a wiping, twisting, dabbing, push/pull, and/or screwing motion around all of the surface aspects of the device to be sterilized.

83 Claims, 18 Drawing Sheets

(56) References Cited

U.S. PATENT DOCUMENTS

| | | | |
|---|---|---|---|
| 4,340,052 A | 7/1982 | Dennehey et al. | |
| 4,354,490 A | 10/1982 | Rogers et al. | |
| 4,366,816 A | 1/1983 | Bayard et al. | |
| 4,405,312 A | 9/1983 | Gross et al. | |
| 4,417,890 A | 11/1983 | Dennehey et al. | |
| 4,432,764 A | 2/1984 | Lopez | |
| 4,440,207 A | 4/1984 | Genatempo et al. | |
| 4,445,896 A | 5/1984 | Gianturco | |
| 4,551,137 A | 11/1985 | Osborne | |
| 4,551,146 A | 11/1985 | Rogers | |
| 4,624,664 A | 11/1986 | Peluso et al. | |
| 4,644,966 A | 2/1987 | Ferrari | |
| 5,063,049 A | 11/1991 | Billings | |
| 5,072,855 A | 12/1991 | Herzig | |
| 5,205,821 A | 4/1993 | Kruger et al. | |
| 5,242,425 A | 9/1993 | White et al. | |
| 5,353,968 A | 10/1994 | Good, Jr. | |
| 5,413,561 A | 5/1995 | Fischell et al. | |
| 5,490,736 A | 2/1996 | Haber et al. | |
| 5,554,135 A | 9/1996 | Menyhay | |
| 5,569,206 A | 10/1996 | Gorman, Jr. et al. | |
| 5,620,527 A * | 4/1997 | Kramer et al. | 134/2 |
| 5,694,978 A | 12/1997 | Heilmann et al. | |
| 5,727,682 A | 3/1998 | Abidin et al. | |
| 5,743,892 A | 4/1998 | Loh et al. | |
| 5,792,120 A | 8/1998 | Menyhay | |
| 5,829,613 A | 11/1998 | Wohlgemuth et al. | |
| 5,989,229 A | 11/1999 | Chiappetta | |
| 6,003,556 A | 12/1999 | Brugger et al. | |
| 6,045,539 A | 4/2000 | Menyhay | |
| 6,116,468 A | 9/2000 | Nilson | |
| 6,416,323 B1 | 7/2002 | Grenfell et al. | |
| 6,517,508 B1 | 2/2003 | Utterberg et al. | |
| 6,764,471 B2 | 7/2004 | Lee | |
| 6,767,509 B1 | 7/2004 | Griesbach | |
| 7,041,083 B2 | 5/2006 | Chu et al. | |
| 7,083,605 B2 | 8/2006 | Miyahara | |
| 7,198,611 B2 | 4/2007 | Connell et al. | |
| 7,282,186 B2 | 10/2007 | Lake, Jr. et al. | |
| 7,294,308 B2 | 11/2007 | Kacian et al. | |
| 7,682,561 B2 | 3/2010 | Davis et al. | |
| 7,763,006 B2 | 7/2010 | Tennican | |
| 7,780,794 B2 | 8/2010 | Rogers et al. | |
| 7,799,010 B2 | 9/2010 | Tennican | |
| 7,972,322 B2 | 7/2011 | Tennican et al. | |
| 8,065,773 B2 * | 11/2011 | Vaillancourt et al. | 15/104.94 |
| 8,162,899 B2 | 4/2012 | Tennican et al. | |
| 8,172,825 B2 | 5/2012 | Solomon et al. | |
| 8,177,761 B2 | 5/2012 | Howlett et al. | |
| 8,197,749 B2 | 6/2012 | Howlett et al. | |
| 8,231,587 B2 | 7/2012 | Solomon et al. | |
| 8,252,247 B2 | 8/2012 | Ferlic | |
| 8,262,643 B2 | 9/2012 | Tennican | |
| 8,273,303 B2 | 9/2012 | Ferlic et al. | |
| 8,328,767 B2 | 12/2012 | Solomon et al. | |
| 8,336,152 B2 | 12/2012 | Vaillancourt et al. | |
| 8,343,112 B2 | 1/2013 | Solomon et al. | |
| 8,388,894 B2 | 3/2013 | Colantonio et al. | |
| 8,628,501 B2 | 1/2014 | Hadden | |
| 8,784,388 B2 | 7/2014 | Charles et al. | |
| 8,828,327 B2 | 9/2014 | Colantonio et al. | |
| 9,078,992 B2 | 7/2015 | Ziebol et al. | |
| 2002/0168530 A1 | 11/2002 | Tingey et al. | |
| 2005/0045031 A1 | 3/2005 | Rajagopalan et al. | |
| 2005/0124970 A1 | 6/2005 | Kunin et al. | |
| 2005/0242204 A1 | 11/2005 | Ness et al. | |
| 2006/0030827 A1 | 2/2006 | Raulerson et al. | |
| 2007/0106205 A1 | 5/2007 | Connell et al. | |
| 2007/0112333 A1 | 5/2007 | Hoang et al. | |
| 2007/0225660 A1 | 9/2007 | Lynn | |
| 2007/0282280 A1 | 12/2007 | Tennican et al. | |
| 2008/0019889 A1 | 1/2008 | Rogers et al. | |
| 2008/0021381 A1 | 1/2008 | Lurvey et al. | |
| 2008/0038167 A1 | 2/2008 | Lynn | |
| 2008/0086091 A1 | 4/2008 | Anderson et al. | |
| 2008/0107564 A1 | 5/2008 | Sternberg et al. | |
| 2008/0132880 A1 | 6/2008 | Buchman et al. | |
| 2008/0177250 A1 | 7/2008 | Howlett | |
| 2008/0235888 A1 | 10/2008 | Vaillancourt et al. | |
| 2009/0028750 A1 | 1/2009 | Ryan et al. | |
| 2009/0137969 A1 | 5/2009 | Colantonio et al. | |
| 2009/0205151 A1 | 8/2009 | Fisher et al. | |
| 2009/0297400 A1 | 12/2009 | Cady et al. | |
| 2010/0000040 A1 | 1/2010 | Shaw et al. | |
| 2010/0003067 A1 | 1/2010 | Shaw et al. | |
| 2010/0050351 A1 | 3/2010 | Colantonio et al. | |
| 2010/0064456 A1 | 3/2010 | Ferlic | |
| 2010/0083452 A1 | 4/2010 | Vaillancourt et al. | |
| 2010/0200017 A1 | 8/2010 | Kerr et al. | |
| 2011/0030726 A1 | 2/2011 | Vaillancourt et al. | |
| 2011/0054440 A1 | 3/2011 | Lewis | |
| 2011/0184382 A1 | 7/2011 | Cady | |
| 2011/0265825 A1 | 11/2011 | Rogers et al. | |
| 2011/0314619 A1 | 12/2011 | Schweikert | |
| 2012/0016318 A1 | 1/2012 | Hoang et al. | |
| 2012/0022469 A1 | 1/2012 | Alpert | |
| 2012/0302997 A1 | 11/2012 | Gardner et al. | |
| 2013/0164189 A1 | 6/2013 | Hadden | |
| 2013/0197485 A1 | 8/2013 | Gardner et al. | |
| 2014/0228773 A1 | 8/2014 | Burkholz | |
| 2014/0261558 A1 | 9/2014 | Rogers et al. | |
| 2015/0343174 A1 | 12/2015 | Ziebol et al. | |

FOREIGN PATENT DOCUMENTS

| | | |
|---|---|---|
| JP | 1284222 A | 11/1989 |
| WO | 2007044760 A2 | 4/2007 |
| WO | 2007137056 A2 | 11/2007 |
| WO | 2008089196 A2 | 7/2008 |
| WO | 2008100950 A2 | 8/2008 |
| WO | 2008140807 A4 | 11/2008 |
| WO | 2009123709 A2 | 10/2009 |

OTHER PUBLICATIONS

The Curos(TM) Port Protector. Simply Changing Infection Control Practice. Printout from http://www.iveramed.com/iv_access_ports_infection_control.html, copyright 2008, originally accessed in 2008, 1 page.

U.S. Appl. No. 13/445,207, filed Apr. 12, 2012.

* cited by examiner

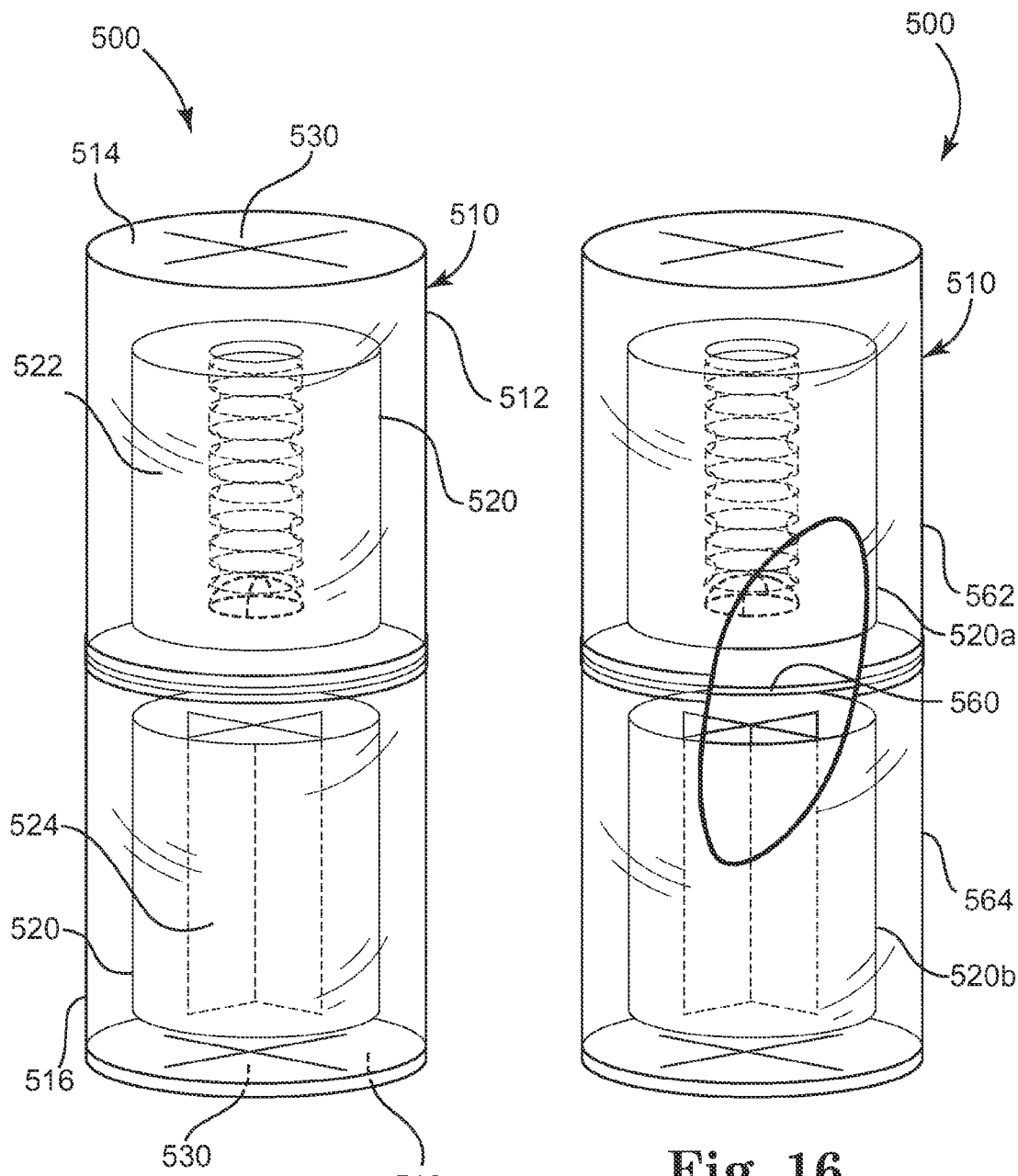

UNIVERSAL STERILIZING TOOL

CROSS-REFERENCE TO RELATED APPLICATIONS

This application is a continuation of U.S. patent application Ser. No. 12/300,717, now U.S. Pat. No. 8,273,303 filed on Sep. 18, 2008, which is a U.S. National Stage Entry of Patent Cooperation Treaty Application No. PCT/US2008/076864, filed on Sep. 18, 2008, which claims the benefit of U.S. Provisional Patent Application Ser. No. 61/050,769, filed on May 6, 2008, the entireties of which are incorporated by reference herein.

TECHNICAL FIELD

The present invention relates to devices and methods for sterilizing the medical connection sites of luer connections, luer compatible components, catheter hubs, and other medical connections and access ports. More particularly, the present invention relates to a contoured sterilizing element that is configured to form-fit to the various shapes and working aspects of the component being sterilized.

BACKGROUND

Mating luer connections, needleless connectors, and needle access ports serve as a conduit for administering medication to a patient by the joining of their mutual complimentary components. Prior to connecting two luer compatible components together, it is important to sterilize the connection end-sites. Typically, the connection end-sites are sterilized by wiping each site with an antiseptic wipe. The wiping and sterilizing of the connection end-sites must be done for a specified amount of time and accuracy to achieve a "kill of microbes" prior to the luer compatible components being connected together to reduce the risk of infection to the patient. This is also true for needle access ports or other connections. Without this simple precautionary step of sterilizing the working end-sites, patients are at a greater risk of contracting an infection.

The current method for sterilizing a connection end-site, catheter hub, needle access port, or needleless connector employs an antiseptic towelette that comes in a small foil packet and is commonly used throughout hospitals, clinics, and home healthcare. The foil packet in which the antiseptic towelette comes in must be torn open and the towelette lifted out with gloved hands. The towelette is a small folded sheet of fibrous, non-woven material that contains isopropyl alcohol. The clinician cannot adequately use the towelette to wipe the various complex surfaces, edges, threads, lumen, septum of a working end-site due to the towelette's small size and flimsy characteristics. Thus, that which should be a routine precautionary step to maintain sterility is unfortunately either ignored or not adequately performed to prevent patient infection.

SUMMARY

According to various embodiments, the present invention is a contoured, pre-moistened anti-pathogenic sterilizing element for wiping medical luer compatible connector end-sites, needleless connector end-sites, and/or needle access port end-sites. According to some embodiments, the sterilizing element is pre-shaped to contour to the outer and inner surfaces of the working end-site of a medical device such that it contacts the outer and inner surfaces of the working site. A wiping and/or a twisting motion is used to wipe debris from and apply a layer of an antiseptic agent to the site. In some embodiments, the sterilizing element is contained in a flexible tubular or rectangular housing.

According to other embodiments, the present invention is a universally adaptable, contoured sterilizing element that is contained within a small ergonomic housing configured to be held in the fingers of one hand. In some embodiments, the housing may be opened by using the fingers of one hand to squeeze the lateral sides, or by forcibly pushing a site end through a sealed membrane or frangible lid to engage the contoured sterilizing element. In other embodiments, the cover can be physically removed from the top of the housing to access the contoured sterilizing element contained within the housing. In other embodiments, the sterilizing element may be left engaged with the working end-site until the end-site is ready for use.

According to some embodiments, the present invention is a sterilizing element for cleaning and sterilizing outer and inner surfaces of a working end-site of a medical device. The sterilizing element includes an anti-pathogenic agent. According to some embodiments, the sterilizing element may be pre-moistened or impregnated with the anti-pathogenic agent. According to other embodiments, the anti-pathogenic agent may be bonded to a surface of the sterilizing element. The sterilizing element includes a first end and a second end and a recessed portion configured to receive the working end-site of the medical device therein. Additionally, the recessed portion includes an inner surface configured to contour to and contact the outer surfaces of the working end-site of the medical device and a raised base portion configured to contact and engage the inner surfaces of the working end-site of the medical device.

According to another embodiment, the sterilizing element includes first and second ends and a recessed portion configured to inwardly receive the working end-site of the medical device. In certain embodiments, the recessed portion includes: a base portion configured to contact a distal end of the working end-site; an inner surface configured to contour and form-fit to the outer surfaces of the working end-site of the medical device; and an inner diameter that tapers down from the first end to the second end of the sterilizing element. According to some embodiments, the sterilizing element may be pre-moistened or impregnated with the anti-pathogenic agent. According to other embodiments, the anti-pathogenic agent may be bonded to a surface of the sterilizing element.

In other embodiments, the present invention is a sterilizing device for wiping and sterilizing outer and inner surfaces of a working end-site of a medical device including a housing and a sterilizing element secured and contained within the housing. In some embodiments, the housing includes at least one end adapted to be opened, and sidewalls having an outer surface. In some embodiments, the sterilizing element includes a first end, a second end, and a recessed portion configured to receive and engage the outer surfaces of the working end-site. In certain embodiments, the recessed portion includes an inner surface configured to contour to and contact the outer surfaces of the working end-site and a raised base portion configured to contact and engage the inner surfaces of the working end-site. According to some embodiments, the sterilizing element may be pre-moistened or impregnated with the anti-pathogenic agent. According to other embodiments, the anti-pathogenic agent may be bonded to a surface of the sterilizing element.

In some embodiments, the at least one end adapted to be opened includes a seal adapted to be transitioned from a closed configuration to an open configuration by the application of an inward pressure applied to the sidewalls of the housing. In other embodiments, the at least one end adapted to be opened includes a lid adapted to be removed from the housing by the application of an inward pressure applied to the sidewalls of the housing.

In certain embodiments, the housing includes an envelope of a flexible material and wherein the at least one end comprises a removable portion. In further embodiments, the housing includes an envelope of a flexible material having a lining, the lining comprising the sterilizing element according to the various embodiments of the present invention.

In some embodiments, the at least one end adapted to be opened includes a frangible lid. According to various embodiments, the frangible lid can be made of plastic, mylar, foil, laminated foil, laminate, or other similar material. In other embodiments, the at least one end adapted to be opened includes a pre-scored lid. In still other embodiments, the at least one end comprises a peel-away lid. According to further embodiments, the housing includes a protective cover secured adjacent to the at least one end adapted to be opened.

In some embodiments, the housing further includes a removable cover secured over the at least one end adapted to be opened. According to some embodiments, the removable cover includes a second sterilizing element contained and secured within the removable cover. The sterilizing element includes a first end and a second end and a recessed portion configured to receive and contact the outer surfaces of the working end-site. The recessed portion includes an inner surface configured to contour to and contact the outer surfaces of the working end-site and a raised base portion configured to contact and engage the inner surfaces of the working end-site. According to some embodiments, the sterilizing element may be pre-moistened or impregnated with the anti-pathogenic agent. According to other embodiments, the anti-pathogenic agent may be bonded to a surface of the sterilizing element.

According to some embodiments, the present invention is a dual-ended sterilizing device including an elongated housing comprising a first portion having a first end adapted to be opened and a second portion having a second end adapted to be opened, and a first sterilizing element contained and secured within the housing. The sterilizing element includes at least one end configured to inwardly receive a working end-site of a medical device therein to conform to and contact at least the outer surfaces of the working end-site. According to some embodiments, the sterilizing element may be pre-moistened or impregnated with the anti-pathogenic agent. According to other embodiments, the anti-pathogenic agent may be bonded to a surface of the sterilizing element.

According to some embodiments, the sterilizing element includes a single, continuous foam piece extending from the first end of the first portion of the housing to the second end of the second portion of the housing. The continuous foam piece generally includes a first end and a second end. Each end of the continuous foam piece is configured to inwardly receive the working end-site therein, and to contour to at least the outer surfaces of the working end-site of the medical device. According to some embodiments, the sterilizing element may be pre-moistened or impregnated with the anti-pathogenic agent. According to other embodiments, the anti-pathogenic agent may be bonded to a surface of the sterilizing element.

According to some embodiments, the dual ended sterilizing device further includes a partition separating the first portion of the housing from the second portion of the housing. The first sterilizing element is secured within the first portion of the housing. In some embodiments, the dual ended sterilizing device includes a second sterilizing element contained and secured within the second portion of the housing. According to various embodiments, the second sterilizing element includes an anti-pathogenic agent and at least one end configured to inwardly receive and conform to at least the outer surfaces of the working end-site. In other embodiments, a sterile drying element can be contained and secured within the second portion of the housing. The sterile drying element can be configured to inwardly receive and conform to at least the outer surfaces of the working end-site. In certain embodiments, the drying element may be left engaged with the working end-site until the site is ready for use. In still other embodiments, the dual ended sterilizing device includes a female luer connector secured to the partition and contained within the second portion of the housing. The female luer connector can be adapted to connect to any one of a male luer lock, slip luer, or thread luer connector.

According to some embodiments, the present invention provides a method of wiping, drying, and sterilizing a medical device including a working end-site having inner and outer surfaces including: providing a sterilizing element comprising an anti-pathogenic agent, and a recessed portion having an inner surface configured to contour to the outer surfaces of the working end-site and a raised portion configured to contact and engage the inner surfaces of the working end-site; inserting the working end-site into the recessed portion of the sterilizing element to engage the working end-site therein; wiping and sterilizing the working end-site located within the recessed portion, removing the working end-site from the sterilizing element, and air-drying the working end-site for a period of time. In some embodiments, the method further includes disposing of the sterilizing element after the initial use.

In some embodiments, the method further includes forcibly engaging the working end-site through the at least one end adapted to be opened to access the sterilizing element contained within the housing. In other embodiments, the method further includes squeezing the sidewalls of the housing to transition the at least one end from a closed configuration to an open configuration to access the sterilizing element contained within the housing. In certain embodiments, the at least one end of the housing may be transitioned from a closed configuration to an open configuration using the fingers on a single hand.

In some embodiments, the method further includes compressing the sterilizing element to expel the anti-pathogenic agent from the sterilizing element and onto the working end-site. In some, the step of compressing the sterilizing element includes engaging the working end-site in the recessed portion of the sterilizing element. In other embodiments, the step of compressing the sterilizing element includes squeezing the sidewalls of the housing to expel the anti-pathogenic agent from the sterilizing element onto the working end-site.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 15 is an isometric view of a dual sided sterilizing device according to another embodiment of the present invention.

FIG. 16 is an isometric view of a dual sided sterilizing device according to yet another embodiment of the present invention.

DETAILED DESCRIPTION

All medical luers and all medical device ends need to be sterilized prior to use. The term "luer" is well known in the medical field and in the art and is used here (luer hub, male luer, female luer, slip luer) to mean mating structures, with or without threads, that allows two mating luer devices, or luer compatible components, to be joined for fluid communication. The term "site," "end-site" or "site end" is used interchangeably and is used here to be understood to mean any and all working ends and/or sites including, but not limited to, a luer, luer hub (e.g. catheter hub), luer compatible component, needle access port, needleless connector, or septum. According to various embodiments, the present invention is a tool for effectively sterilizing and wiping debris from all surfaces of a working end including, but not limited to, threads, sides, edges, inner lumens, septums, and needle access ports.

Figure 1:
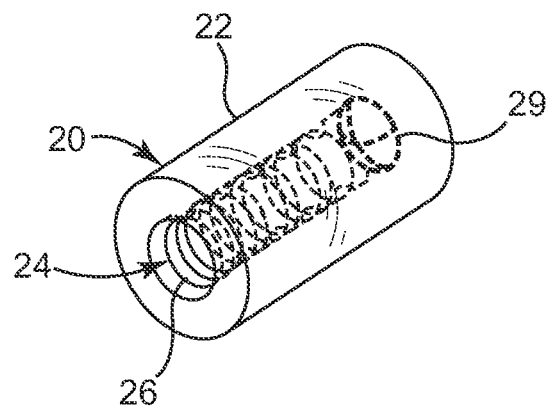
FIG. 1 is an isometric view of a contoured sterilizing element provided in accordance with an embodiment of the present invention.
Figure 2A:
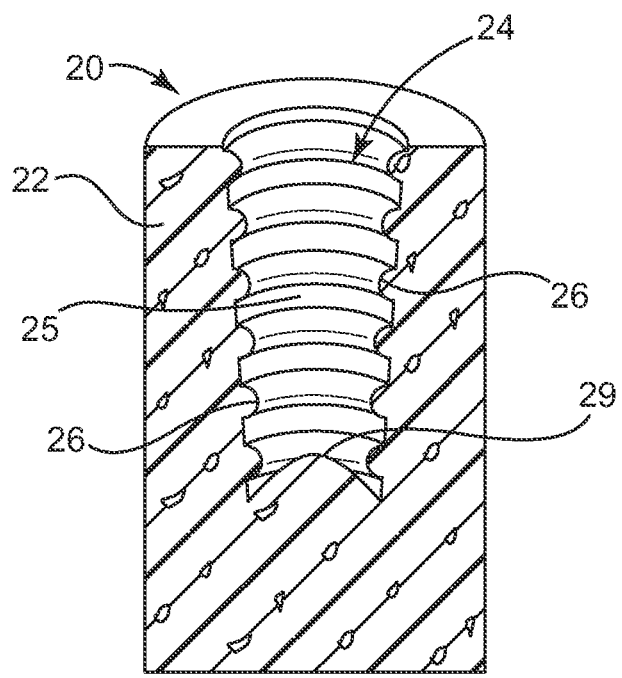
FIG. 2A-2C are cross-sectional views of a contoured sterilizing element in accordance with various embodiments of the present invention.
Figure 2B:
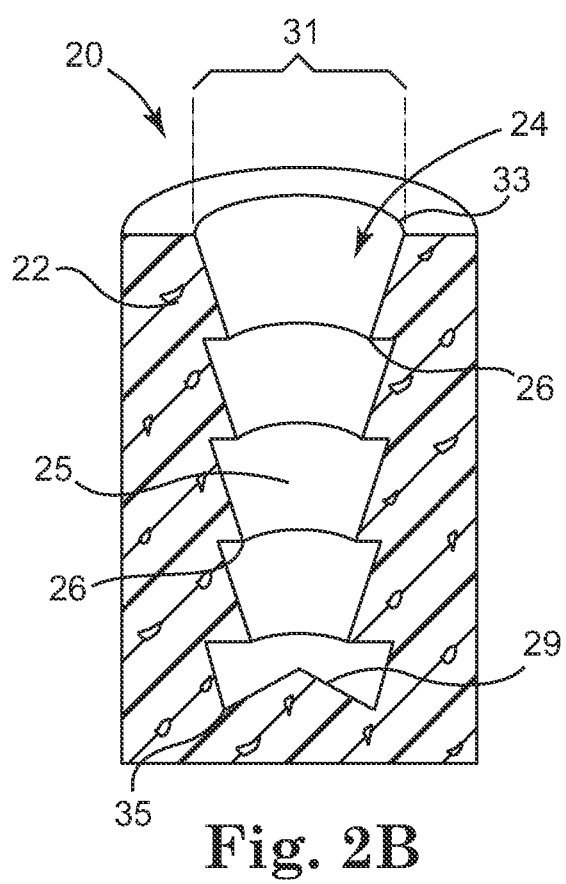
Figure 2C:
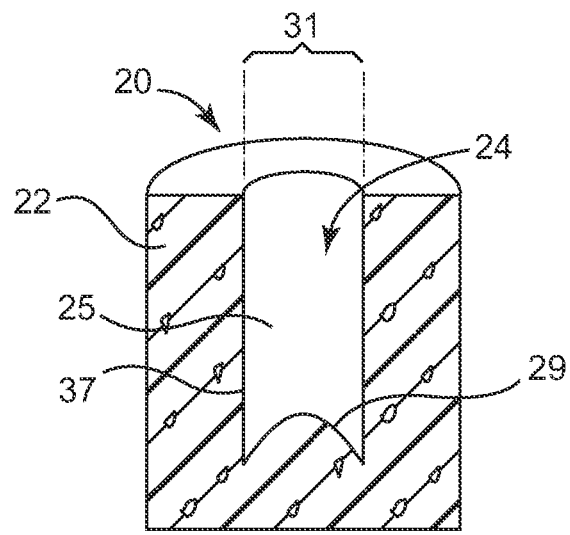

FIG. 1 is an isometric view of a contoured sterilizing element 20 provided in accordance with various embodiments of the present invention. FIGS. 2A-2C are cross-section views of the contoured sterilizing element 20, as shown in FIG. 1, according to various embodiments of the present invention. The sterilizing element 20 is configured to wipe debris from and to sterilize and/or dry a working end-site of a catheter hub, luer connector, luer component, and/or access port using a wiping, twisting, dabbing, push/pull and/or screwing motion around all of the surface aspects of the device to be sterilized. Additionally, the sterilizing element 20 is configured to apply an inclusive layer of an anti-pathogenic agent to the inner and outer surfaces of the working end-site. An inclusive layer, as used herein, is a layer of the anti-pathogenic agent applied via the contoured aspects of the sterilizing element which contacts all accessible inner and outer surfaces of the working end-site and contains an amount of the pathogenic agent sufficient to effectively sterilize the working end-site of the medical device. The contoured sterilizing element 20 is intended for a one time, single use, disposable application.

The sterilizing element 20 can be made from a variety of materials including, but not limited to, non-woven, particulate-free absorbent foams, natural or synthetic sponges, or other suitable materials, both semi-flexible or semi-ridged, known to those of skill in the art. In some embodiments, the contoured sterilizing element 20 includes an absorbent foam article 22. In other embodiments, the contoured sterilizing element 20 is formed from an absorbent, viscoelastic or resilient foam.

According to some embodiments, the absorbent material can be pre-shaped or pre-molded such that it is configured to contour to the surfaces of the working end to be sterilized. For example, in some embodiments, the sterilizing element 20 can be contoured and pre-shaped such that it is configured to form-fit over the working end-site of a medical connector, catheter hub, luer compatible connector, luer component, and/or needle access port for efficient wiping and sterilizing. In other embodiments, the sterilizing element 20 can be shaped to contour to and engage an inner lumen, septum, port, and/or needleless injection site. In yet other embodiments, the sterilizing element 20 is configured to engage a working end-site of a medical device such that a friction fit is created between the sterilizing element 20 and the end-site of the medical device. The sterilizing element 20 can remain frictionally engaged with the working end-site until ready for use. According to another embodiment, the absorbent foam material is sufficiently resilient such that it conforms to the surfaces of the working end-site when the working end-site is depressed into the absorbent material.

According to various embodiments, the absorbent material includes an anti-pathogenic agent including any one of an antiseptic, disinfectant, microbiocidal, or combinations thereof to kill pathogens on the surfaces of the device. According to one embodiment, an anti-pathogenic agent is a dry agent bonded to the surfaces of the sterilizing element. According to another embodiment, the sterilizing element is impregnated with an anti-pathogenic agent. For example, the sterilizing element may be impregnated with an oligodynamic metal. An oligodynamic metal is a metal shown to have anti-bacterial properties even in minute quantities. Exemplary oligodynamic metals include, but are not limited to, the following: gold, zinc, copper, and cerium. According to one embodiment, the sterilizing element may be impregnated with silver. In other embodiments, the absorbent material is pre-moistened with at least one anti-pathogenic agent. Exemplary anti-pathogenic agents include, but are not limited to, the following: isopropyl alcohol, povidone iodine, chlorhexidine gluconate, and other useful anti-pathogenic agents known to those of skill in the art. Additionally, depending on the anti-pathogenic agent used, a sufficient amount of anti-pathogenic agent can be incorporated into the absorbent material to achieve an acceptable ratio of "anti-pathogenic agent to dry-time," wherein a sufficient amount of anti-pathogenic agent is used to adequately disinfect the site end while at the same time achieving a fast drying rate. The connector devices should be sterile, dry, and free of antiseptic residue since they complete the pathway of medication into the patient's body prior to their connection. According to one embodiment, the drying rate after the anti-pathogenic agent has been applied to the working end-site is less than about 15 seconds. In other embodiments, the drying rate is less than about 10 seconds. In still other embodiments, the drying rate is less than about 7 seconds.

FIGS. 2A-2B are cross-sectional views of a sterilizing element 20, according to various embodiments of the present invention. According to some embodiments, the contoured sterilizing element includes an absorbent foam piece 22 having a recessed portion 24 including an inner surface 25 configured for receiving the working end-site of a medical device to be sterilized therein. According to one embodiment, the recessed portion 25 is configured such that the working end-site can be inserted to a depth of approximately 10 mm. In other embodiments, the recessed portion 25 is configured such that the working end-site can be inserted into the recessed portion 25 by a depth of about 5 mm to about 7 mm. In yet another embodiment, the working end-site may be inserted into the recessed portion 25 by a depth of about 3 mm.

As shown in FIGS. 2A and 2B, the recessed portion 24 can include a plurality of raised structures 26 formed on the inner surface 25 of the recessed portion 24. The raised structures 26 project into the recessed portion, and are configured to engage the threads, sides, and/or edges on the working end-site. In some embodiments, the raised structures 26 can include ridges, flanges, and/or threads, as shown in FIG. 2A, steps as shown in FIG. 2B, or combinations thereof. According to a further embodiment, as shown in FIG. 2B, the raised structures 26 provided on the inner surface 25 of the recessed portion 24 provide an inner diameter 31 that tapers down from a first end 33 to a second end 35 of the sterilizing element 20. These raised structures 26 located on the inner surface 25 of the recessed portion or cavity 24 of the sterilizing element 20 facilitate the effective sterilization of all surfaces of the working end-site of a first connection device prior to the attachment with a complimentary second connection device.

Additionally, in some embodiments the recessed portion 24 can include a raised base portion 29 configured to project into and engage the inner luer lumen and/or septum of a needleless connector or port end. The raised base portion can have a number of configurations. For example, the raised base portion 29 can be configured as any one of a nipple, bump, nub, tine, or other similar projection.

FIG. 2C is a cross-sectional view of a sterilizing element 20 according to yet another embodiment of the present invention. As shown in FIG. 2C the sterilizing element 20 includes a generally, cylindrical absorbent foam piece 22 having a recessed portion 24. The cylindrical foam piece 22 can be contoured and shaped so that it "form-fits" over the working end-site of a luer compatible connector, medical device connector component, and/or needle access port for efficient wiping and sterilizing. In one embodiment, as shown in FIG. 2C, the recessed portion 24 has an inner diameter 31 less than an outer diameter of the working end-site to be sterilized such that when a working end-site is received in the recessed portion 24 the inner walls 37 of the recessed portion conform to the outer surfaces of the working ends site. In some embodiments, the sterilizing element 20 may include a raised base portion 29 configured to project into and engage the surfaces of an inner lumen or septum, as described above.

Figure 3:
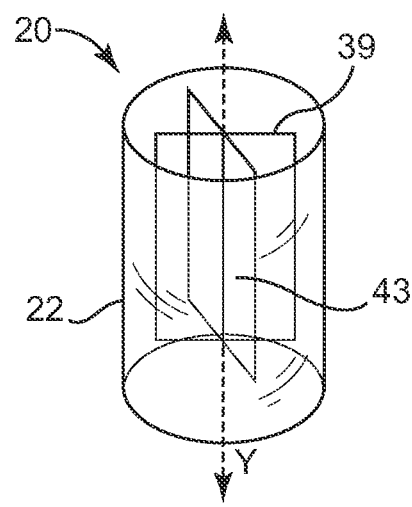
FIG. 3 is an isometric view of a sterilizing element according to another embodiment of the present invention.

FIG. 3 is an isometric view of a sterilizing element 20 according to another embodiment of the present invention. The sterilizing element 20 is made from a foam or sponge-like material and is die cut to conform to the surfaces of the working end-site to be sterilized. The die cut sterilizing element 20 can be cut in a number of configurations, such that it conforms to a variety of medical device connectors, components, and access ports. Additionally, according to some embodiments, the die cut sterilizing element 20 can be cut such that it is especially configured to accommodate a device having a lumen or septum. For example, the die cut sterilizing element 20 may be cut such that it is configured to project into and engage the inner surfaces of the a medical device having an inner lumen and/or a septum. In one embodiment, as shown in FIG. 3, the sterilizing element 20 includes an absorbent foam piece 22 that is die-cut to include at least one slit 39 formed along a longitudinal axis Y of the element 20 such that when a working end-site is depressed into the sterilizing element 20, the slit 39 opens to receive the working end-site therein. The slit 39 includes side walls 43 configured to conform to the surfaces of the working end-site to be sterilized.

Figure 4:
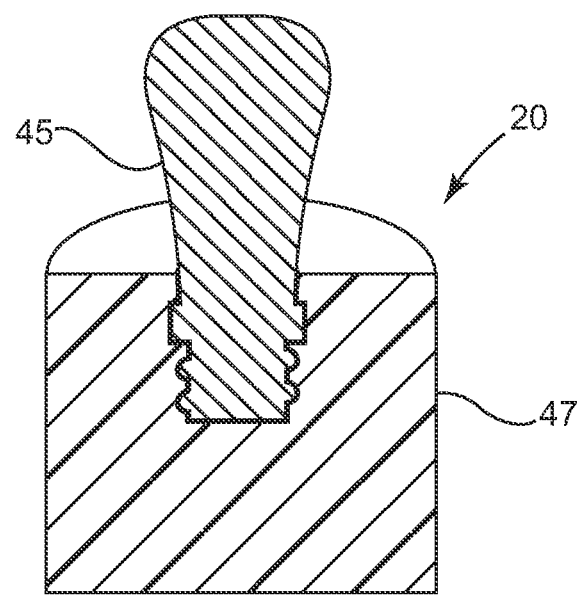
FIG. 4 is a cross-sectional view of a contoured sterilizing element engaged with a thread luer connector.

FIG. 4 is a cross-sectional view of a sterilizing element 20, according to yet another embodiment of the present invention, including a working end-site 45 of a device to be sterilized received therein. As shown in FIG. 4, the sterilizing element 20 includes an absorbent, resilient article 47. In one embodiment, the absorbent resilient article 47 is fabricated from a viscoelastic foam (e.g. viscoelastic polyurethane foam). The absorbent, resilient article 47 has sufficient resiliency such that when the working end-site 45 is pressed into the resilient article 47, the resilient article 47 depresses to receive the working end-site 45 to a depth sufficient for the effective wiping and sterilization of the working end-site 45. Additionally, when the working end-site 45 is pressed into the resilient article 47 to a sufficient depth, the depressed resilient article 47 conforms to the outer surfaces of the working end-site 45.

The sterilizing element 20, according to the various embodiments, described above may be formed using a variety of techniques. According to one embodiment, the sterilizing element 20 may be heat-set, molded, pressure-molded, injection-molded, cored, laser, and/or die cut. Other techniques known to those of skill in the art for forming and shaping foam may also be used.

Figure 5A:
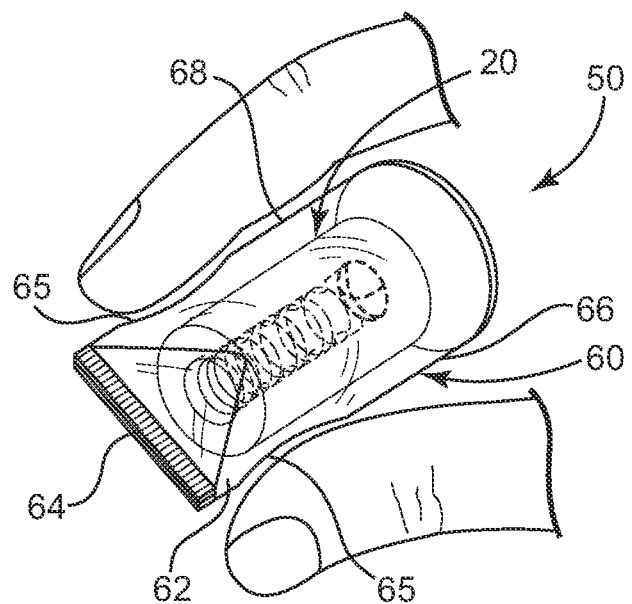
FIGS. 5A and 5B are isometric views of a sterilizing device according to one embodiment of the present invention.
Figure 5B:
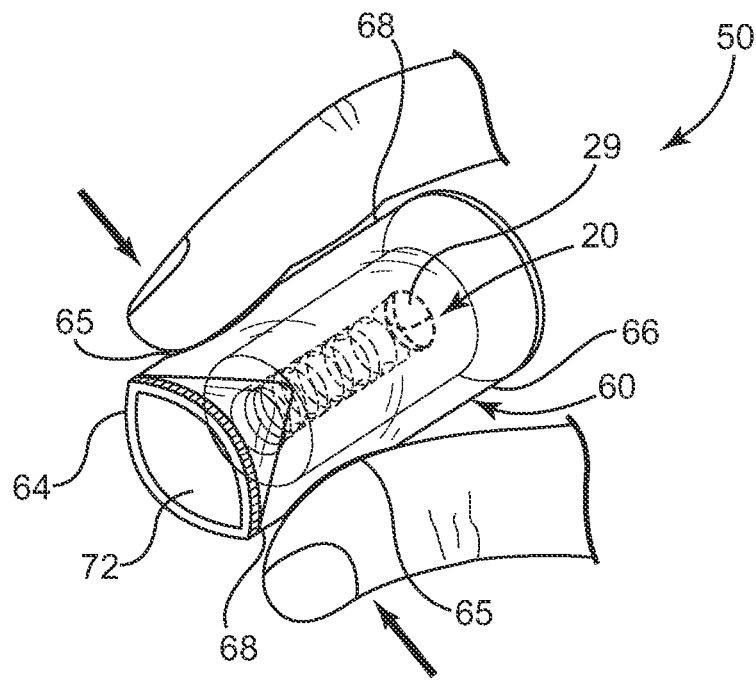

FIGS. 5A and 5B are isometric views of a sterilizing device 50 according to various embodiments of the present invention. As shown in FIGS. 5A and 5B, the sterilizing device 50 includes a sterilizing element 20, such as described above, according to the various embodiments, contained within a housing 60. According to some embodiments, the sterilizing element 20 is contained within the housing 60 such that the housing 60 provides a barrier to direct contact with the sterilizing element 20 when the sterilizing element 20 is in use, and serves as a tool for mechanically manipulating the sterilizing element 20. According to various embodiments, as will be described in further detail below, the housing 60 can include a top or lid to seal and protect the pre-moistened sterilizing element from drying out within the housing until it is ready for use.

The sterilizing element 20 is secured within the housing 60 to prevent dislodgement of the sterilizing element 20 from the working end-site of the device being sterilized. The sterilizing element 20 should be sufficiently secured within the housing 60 such that it can withstand vigorous wiping of an end-site. The sterilizing element 20 can be secured within the housing by various methods including, but not limited to, the following: ultrasonic welding, inward indentations of the walls, internal molded ribs or points, adhesives, frictional engagement, as well as the sterilizing element's own outward expanding radial force to hold it in place within the housing.

According to other embodiments, the sterilizing element 20 may be removed from the housing for attachment to the end-site, as well as be directly held by the gloved hand of the user. Additionally, the contoured sterilizing element 20 may be left in place within the housing and the whole device can be left on the end-site for the purpose of protecting the site's sterility until such time the device is removed so that the site end can be used.

According to various embodiments, the housing 60 is small and ergonomically shaped so as to be easily held within the fingers of one hand of the user. In certain embodiments, the housing 60 is configured to be opened single handedly using the fingers on one hand. Additionally, the housing 60 can have a general shape such as an hourglass or flared shape that guides the placement of a user's fingers. According to other embodiments, the housing 60 can include one or more fingers locating features 65 formed with sidewalls 66 and 68 of the housing 60 to guide a user's placement of their fingers when using the device 50. The finger locating features 65 may also facilitate gripping and handling of the device by the user. According to various embodiments, the finger locating features 65 can include but are not limited to be dimples, bumps, grip marks, and other features useful for locating a user's fingers. As shown in FIGS. 5A and 5B the finger locating features 65 include recesses formed in the sidewalls 66 and 68 of the housing 60. According to some embodiments, the housing 60 can be opened using the fingers on a single hand.

The housing 60 is sized to receive the working end-site of a medical connection inserted therein. The medical device or working end-site is inserted into the housing to access the sterilizing element 20 contained therein. According to one embodiment, the housing 60 is configured such that the working end-site can be inserted to a depth of approximately 5 mm. In other embodiments, the housing 60 is configured such that the working end-site can be inserted into the housing 60 by a depth of about 3 mm to about 5 mm. In yet another embodiment, the working end-site may be inserted into the housing by a depth of about 4 mm.

The housing 60 can be made from a variety of materials. According to some embodiments, the housing 60 is made from a plastic, laminated paper/foil combination, or other semi-rigid material or semi-flexible material. As shown in FIG. 5A, a top portion 62 of the housing 60 can be pinched closed to form a seal 64. The seal 64 may be formed using ultrasonic welding, heat thinning and/or a liquid impermeable polyolefin film forming a combination molded seam and parting seal. As shown in FIG. 5B, the user squeezes the sidewalls 66 and 68 of the housing 60 inward with the fingers of one hand such that the seal 64 formed along the top portion 62 opens to form opening 72. The opening 72 is sized to receive the working end-site of a connection device or other medical device therein. In some embodiments, the squeezing action causes an audible "popping sound" as the seal 64 is forced open. Opening the seal 64 exposes the sterilizing element 20 secured within the housing 60 and allows for receipt therein of the working end-site of the connection device or other medical device to be sterilized.

Figure 6:
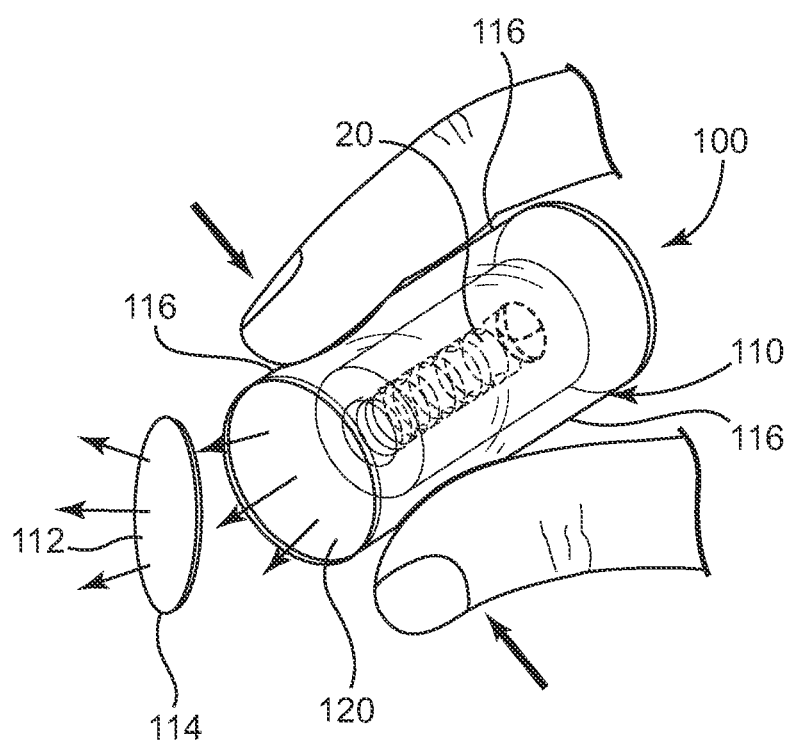
FIG. 6 is an isometric view of a sterilizing device according to another embodiment of the present invention.

FIG. 6 is an isometric view of a sterilizing device 100 including a pre-moistened sterilizing element 20 contained within a housing 110 according to another embodiment of the present invention. The sterilizing element 20 can have any configuration according to the various embodiments, as described above. As shown in FIG. 6, the housing 110 shows a frangible top 112 that can be sealed onto the housing 110 utilizing a combined molded seam and parting seal 114. The top 112 is secured to the housing 110 such that when the user squeezes the sidewalls 116 of the housing 110 with the fingers of one hand, the seal along the top 114 releases due to an increase in internal pneumatic pressure causing the top 112 to pop off and detach from the housing 110 to create an opening 120 facilitating access to the sterilizing element 20 contained inside.

Figure 7A:
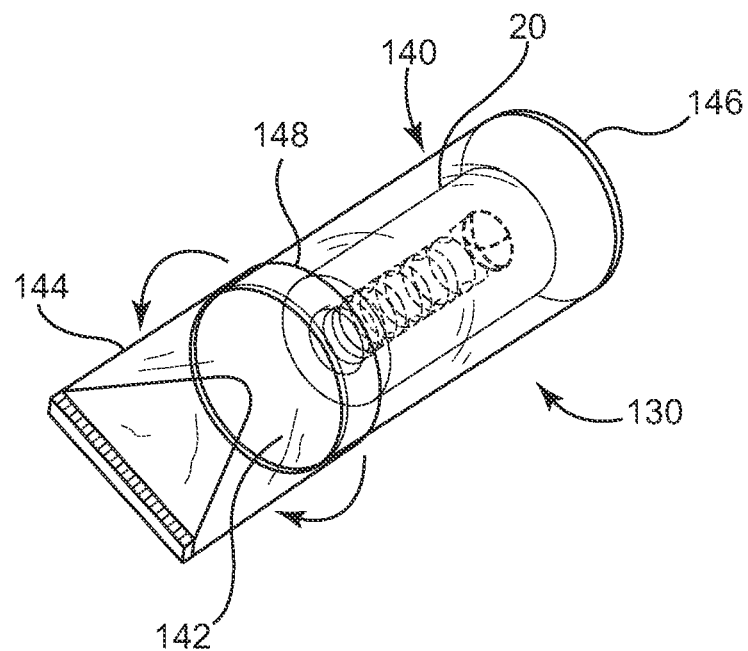
FIG. 7A is an isometric view of a sterilizing device including a housing having a removable cover according to still another embodiment of the present invention.
Figure 7B:
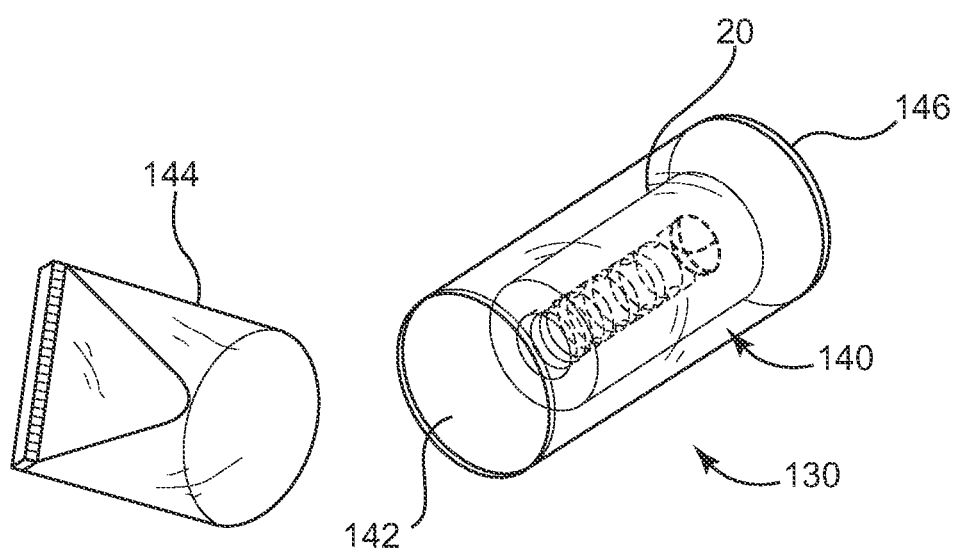
FIG. 7B is an isometric view of the sterilizing device shown in FIG. 7A, wherein the housing cover is removed.

FIGS. 7A and 7B are isometric views of a sterilizing device 130 according to another embodiment of the present invention. The sterilizing device 130 includes a pre-moistened sterilizing element 20 contained within a housing 140 having an opening 142, sized to receive the working end-site of a medical device. The sterilizing element 20 can have any configuration according to the various embodiments, as described above. The housing 140 includes a removable cover 144. As shown in FIG. 7A, the removable cover 144 can be secured to the housing 140 via a circumferential frangible tear line 148. As shown in FIG. 7B, the cover 144 can be removed using a twisting and pulling motion to detach the cover 144 from the housing 140 via the tear line 148. In some embodiments, the cover 144 and the body 140 can be made of plastic, mylar, foil, laminated foil, or other flexible material. In other embodiments, the cover 144 can be made of a semi-flexible or semi-rigid material.

Figure 8:
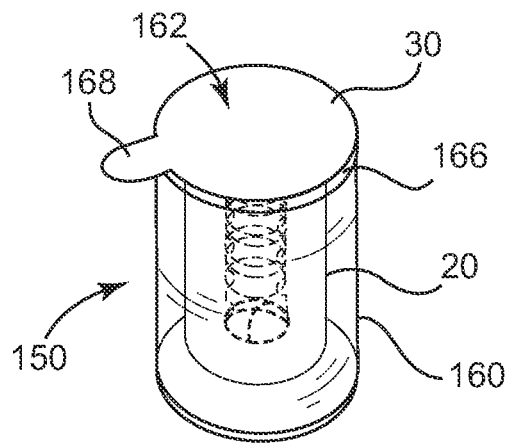
FIG. 8 is an isometric view of a sterilizing device including a housing having a removable lid provided in accordance with an embodiment of the present invention.
Figure 9:
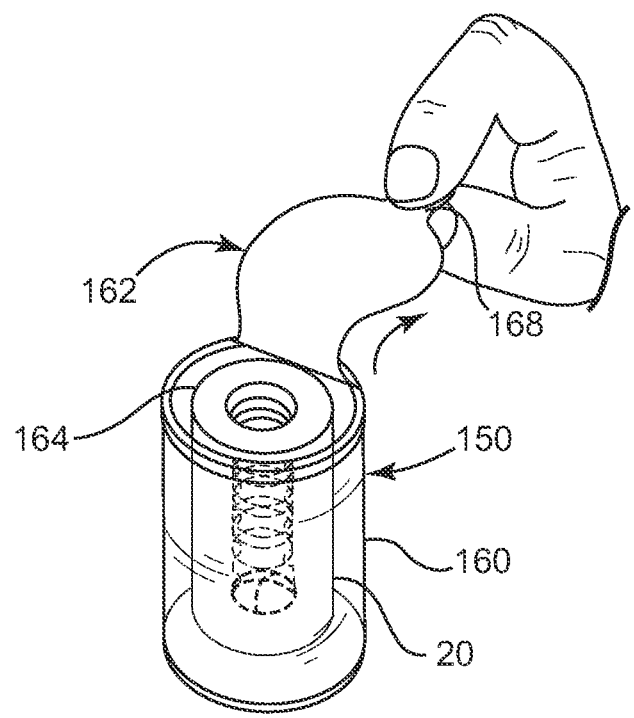
FIG. 9 is an isometric view of the sterilizing device shown in FIG. 8, wherein the lid is removed.

FIGS. 8 and 9 are isometric views of a sterilizing device 150 including a pre-moistened sterilizing element 20 contained within a housing 160 having a removable cover 162 according to another embodiment of the present invention. The sterilizing element 20 can have any configuration according to the various embodiments, as described above. According to one embodiment, the removable cover 162 is a peel-away lid. As shown best shown in FIG. 8, the cover 162 is secured over the top opening 164 of the housing 160 such that it seals the pre-moistened sterilizing element 20 within. The cover 162 includes a circumferential tear line 166 for facilitating its removal. Additionally, the cover 162 can also include a tab or tether 168. According to one embodiment, as shown in FIG. 9, a user manually grasps the tab or tether 168 and pulls the cover 162 from the housing via the tear line 166 to reveal the opening 164 and grant access to the sterilizing element 20 contained within.

Figure 10:
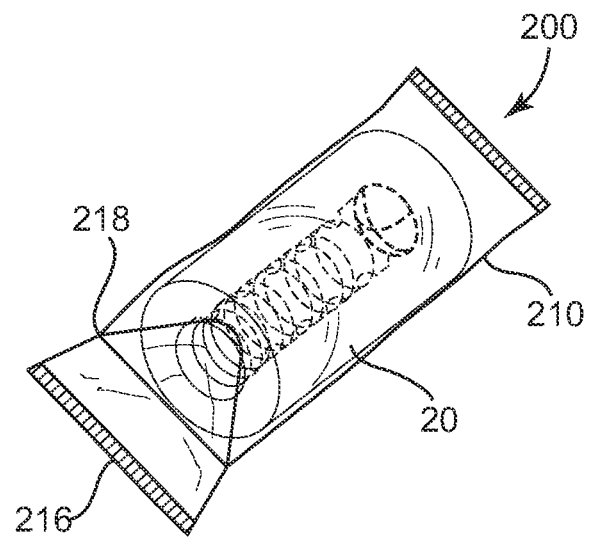
FIG. 10 is an isometric view of a sterilizing device including a housing having a tear off end provided in accordance with an embodiment of the present invention.
Figure 11:
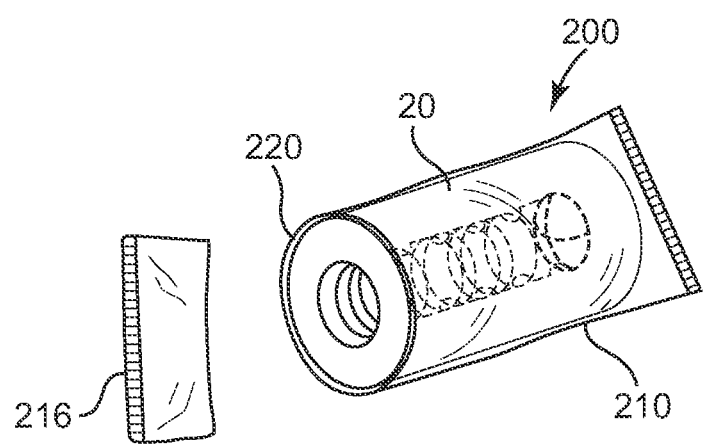
FIG. 11 is an isometric view of the sterilizing device shown in FIG. 10, wherein the end is removed.

FIGS. 10 and 11 are isometric views of a sterilizing device 200 including a pre-moistened sterilizing element 20 contained within a flexible envelope housing 210 according to yet another embodiment of the present invention. The sterilizing element 20 can have any configuration according to the various embodiments, as described above. The flexible envelope housing 210 may be formed from plastic, mylar, foil, laminated, or other flexible material. According to a further embodiment, the flexible envelope housing 210 may include a foil lining to further maintain the moisture level of the sterilizing element contained within. As shown in FIGS. 10 and 11, the flexible envelope housing 210 includes a removable protective cover 216. The removable protective cover 216 can include a line of perforations or weakness 218 configured to facilitate removal of the protective cover 216 from the housing 210. The removable protective cover 216 may be removed from the housing by tearing or cutting along the line 218. FIG. 11 shows the protective cover 216 removed from the housing 210 to create an opening 220 facilitating access to the sterilizing element 20 contained within.

Figure 12:
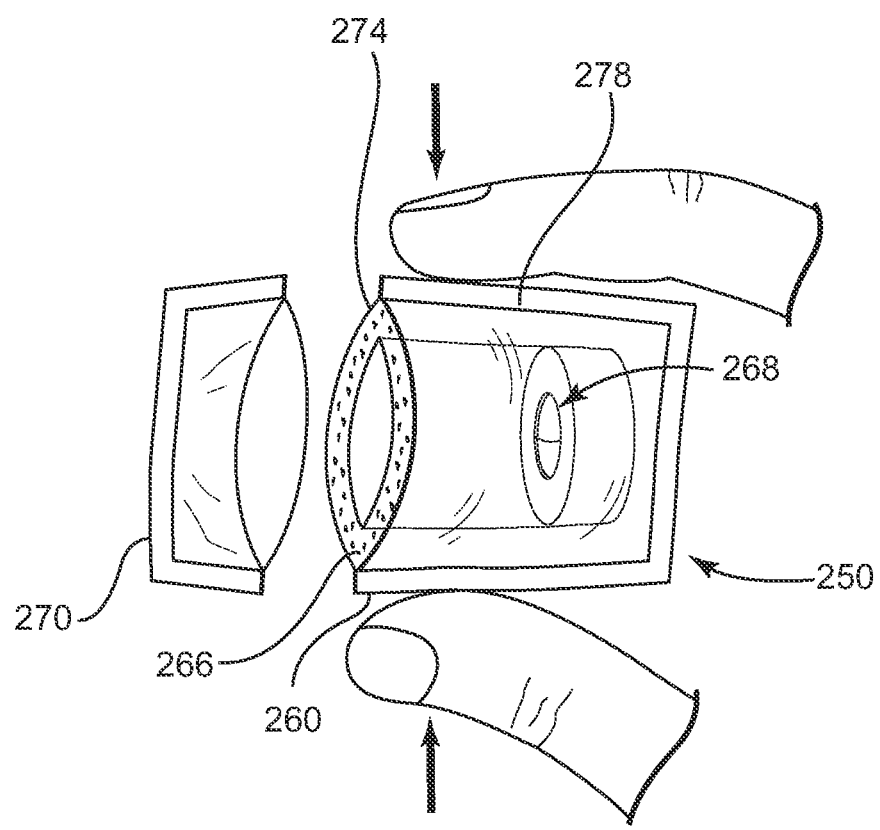
FIG. 12 is an isometric view of a sterilizing device according to yet another embodiment of the present invention.

FIG. 12 is an isometric view of sterilizing device 250 according to another embodiment of the present invention. The sterilizing device 250 includes a flexible envelope housing 260 including an inner lining 266 and a removable protective cover 270. In some embodiments, the removable protective cover 270 can be removed from the housing 260 by tearing or cutting along a perforation line or other similar line of weakness. The protective cover 270 is shown removed from the housing 260 in FIG. 12.

The inner lining 266 can be made of a particulate free absorbent foam or sponge-like material. The absorbent foam or sponge-like material is pre-moistened with an anti-pathogenic agent, as previously described above and lines the inner walls of the envelope housing 260. The inner foam lining 266 is contoured and can include a plurality of raised ridges, ribs or threads configured to engage the threads, sides, and/or edges on the working end-site. Additionally, as shown in FIG. 12, the inner foam lining 266 includes raised base 268 configured to project into and to engage the inner luer lumen and/or septum of a needleless connector or port end. Additionally, according to a further embodiment, the inner lining 266 can include a reinforced oval rim 274. The reinforced oval rim 274 is adapted to flex from a closed position to an open position by squeezing the sides 278 of the flexible envelope housing 260 upon removal of the protective cover 270. The rim 274 is flexed open to facilitate the reception of a working end-site of a device to be sterilized within the inner lining 266 of the envelope 260.

Figure 13A:
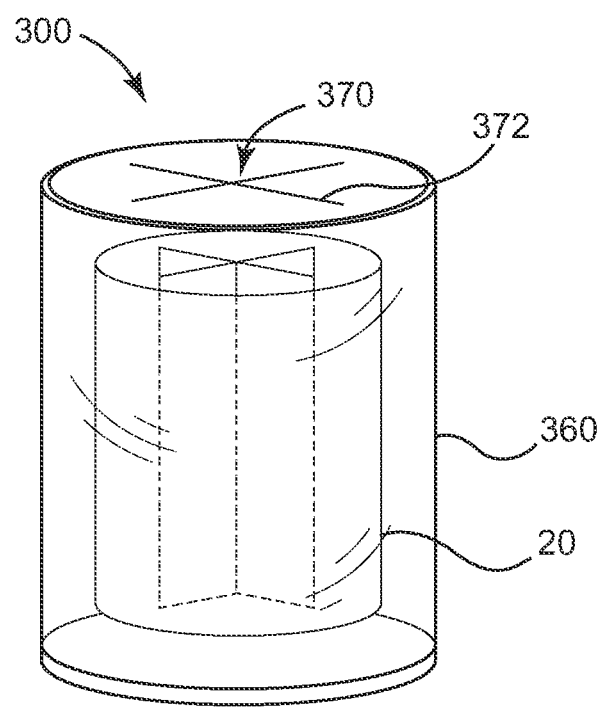
FIG. 13A is an isometric view of a sterilizing device including a frangible top according to an embodiment of the present invention.
Figure 13B:
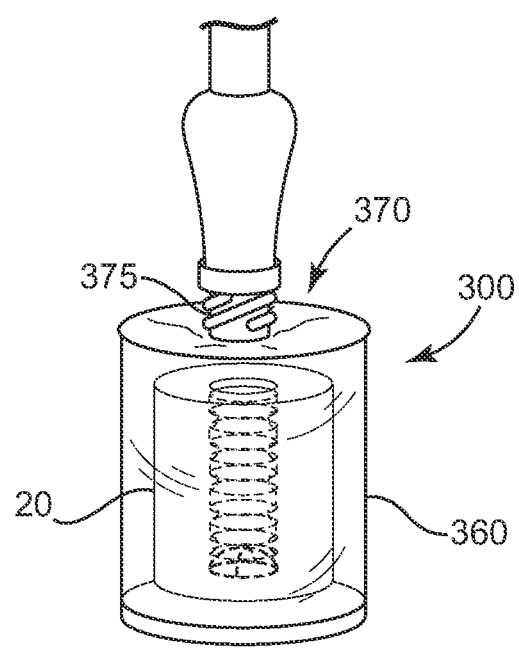
FIG. 13B is an isometric view of a working end-site forcibly engaged through the frangible top of a sterilizing device.

FIG. 13A is an isometric view of a sterilizing device 300 including a sterilizing element 20 contained within a generally cylindrical housing 360. The sterilizing element 20 can have any configuration according to the various embodiments, as described above. According to one embodiment, the housing 360 includes a frangible lid 370. The lid 370 seals the pre-moistened sterilizing element 20 and maintains a moisture rich environment inside the housing 360. According to various embodiments, the frangible lid 370 can be made of plastic, mylar, foil, laminated foil, laminate, or other similar material. In some embodiments, the frangible lid may include score-marks 372 to facilitate breaking of the frangible lid 370. The frangible lid 370 should be of sufficient thickness and frangibility, that the working end-site 375 (as shown in FIG. 13B) of a device to be sterilized, can penetrate the lid by forcibly engaging the working end-site through the pre-scored lid to access the sterilizing element 20 contained within the housing 360. FIG. 13B shows a working end-site of a device to be sterilized forcibly engaged through the frangible top 370 of the sterilizing device 300.

In some embodiments, the housing 360 is sized to facilitate prolapse of the frangible lid 370 into the housing 360. For example, as the working end-site 375 is being forcibly engaged through the frangible lid 370, the lid material pushes inward and down into the housing 360 such that the working end-site 375 can access and engage the sterilizing element 20 contained within the housing 360. In some embodiments, the working end-site 375 can be left engaged with the sterilizing element 20 contained within the housing 360 until the end-site 375 is ready for use. Together with the lid 370, the housing 360 and the sterilizing element 20 have sufficient integrity and durability such that the device 300 resists removal of the end-site 375 from the device 300 thus allowing the device 300 to be left engaged with the end-site 375 without the potential for inadvertent disengagement from the device 300. According to one embodiment, the housing 360 provides a depth of less than about 10 mm to facilitate prolapse of the lid 370 into the housing 360. In another embodiment, the housing 360 provides a depth of about 5 mm to about 10 mm, of about 3 to about 5 mm, and/or about 4 mm to facilitate prolapse of the lid 370 into the housing 360.

Figure 14:
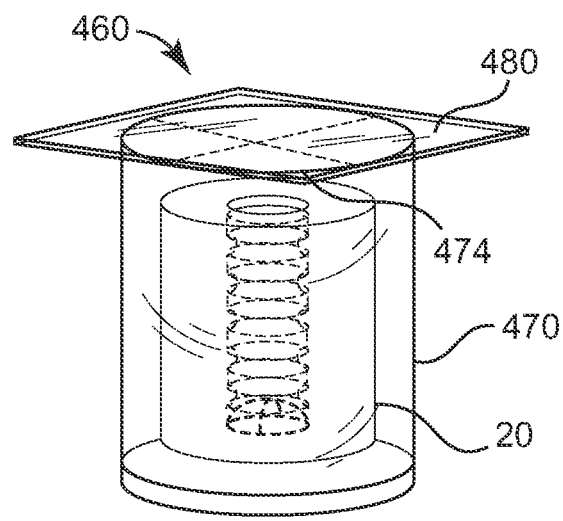
FIG. 14 is an isometric view of a sterilizing device including a protective cover according to other embodiments of the present invention.

FIG. 14 shows a sterilizing device 460 according to a further embodiment of the present invention. As shown in FIG. 14, the sterilizing device 460 includes a pre-moistened sterilizing element 20 according to the various embodiments as described above, contained within a housing 470 having a lid 474 and an additional debris protective covering 480. The lid 474 is secured to the top of the housing 470 to seal the pre-moistened sterilizing element 20 within the housing. According to one embodiment, as previously described above, the lid 474 is a foil or plastic frangible lid and may be pre-scored to include score-marks. Additionally, the lid 474 is of sufficient thickness and frangibility such that a working end-site of a device to be sterilized can be forced through the lid 474 to access the sterilizing element 20 contained within the housing 470.

The debris protective covering 480 is positioned adjacent and secured to the lid 474. The debris protective covering assists in keeping the device lid 474 free of debris until the device is ready for use. The debris protective covering 480 extends outward beyond an outer diameter of the housing 470. This configuration helps to stabilize the device 460 and may prevent it from rolling when the device 460 is placed on its side. Additionally, the configuration may provide a wider, sturdier base for the device 460, if the device is placed top-side-down on a flat surface. The debris protective covering 480, as shown in FIG. 14, can be used in conjunction within a variety of housing configurations, such as those described above.

FIG. 15 is an isometric view of a dual sided sterilizing device 500 according to yet another embodiment of the present invention. As shown in FIG. 15 the dual sided sterilizing device 500 includes an elongated ergonomic housing 510, having a first end 512 including a first opening 514 and a second end 516 including a second opening 518. At least one sterilizing element 520 is located within the housing 510 and can be accessed through either the first or second opening 514 or 518.

According to one embodiment, the housing 510 includes a seal or lid 530 located over each of the first and second openings 514 and 518. The lid or seal 530 can have any one of the configurations as described above. According to one embodiment, as shown in FIG. 15, the lid 530 can be a pre-scored lid. According to further embodiments each of the first and second ends 512 and 516 can include a plastic, foil, or laminated lid 530 that is of sufficient thickness and frangibility that a working end-site of a device to be sterilized can be forced through the lid to gain access to the sterilizing element contained inside. In some embodiments, a protective covering, such as described above with reference to FIG. 14, may be secured to the lid 530.

According to various embodiments, the dual sterilizing element 520 contained within the housing 510 can be made from a non-woven, particulate free absorbent foam, or sponge-like material. The absorbent foam or sponge-like material is pre-moistened with an anti-pathogenic agent including any one of an antiseptic, disinfectant, microbiocidal, or combinations thereof to kill pathogens on the surfaces of the device. Additionally, the sterilizing element 520 is contoured and shaped so that it "form-fits" over the working end-site of a luer compatible connector, device, and/or needle access port for efficient wiping and sterilizing. According to one embodiment, the sterilizing element 520 can extend continuously from the first end 512 to the second end 516 throughout the entire housing length 510. According to another embodiment, described in further detail below, the sterilizing element 520 can include two separate portions contained within the housing 510.

Like the housing 510, the dual sterilizing element 500 includes a first end 522 and a second end 524. Each end 522 and 524 can be shaped to fit to the various male, female (inner lumen), slip luer, septum, port, or threaded configurations of a working end-site to be sterilized, and apply an inclusive layer of an anti-pathogenic agent to sterilize and wipe debris from the site while using a wiping and twisting motion. According to one embodiment, each end 522 and 524 can have the same contouring. According to another embodiment, the first end 522 and the second end 524 can have different contouring. For example, the first end 522 can be contoured such that it contacts and engages the surfaces of a male connection component (e.g. male luer lock or a slip luer) and the second end 524 can be contoured such that it projects into and engages the surfaces of various female (inner lumens) and/or septums (e.g. a needleless injection port).

According to further embodiments, each of the first and second ends 514 and 518 can include a label (not shown) located on an outer surface of the housing 510. The label can be embossed or printed with differentiating numbers, letters, or symbols to assist the clinician in identifying which end of the housing they are using. Using labels to identify the working ends 514 and 518 is useful, for example, when the first and second ends 522 and 524 of the sterilizing element 520 differ so as to be used to clean and sterilize different medical devices. Additionally, labels to identify the working ends 514 and 518 of the device 500 are also useful when the anti-pathogenic agents on the first and second ends 522 and 524 of the sterilizing element 520 differ such that the anti-pathogenic agent can be selected depending on the material to be sterilized. In certain embodiments, when the sterilizing device 500 is left engaged with the working end-site after it has been cleaned and sterilized, a label can be used to signify to the user or users that the connection has been sterilized and is ready for use.

FIG. 16 is a schematic view of the dual sided sterilizing device 500 shown in FIG. 15 according to another embodiment of the present invention. According to one embodiment, as shown in FIG. 16, a divider or partition 560 separates the device into two distinct portions 562 and 564. According to this embodiment, each of the portions 562 and 564 contain a separate sterilizing element 520a or 520b. The sterilizing elements 520a and 520b are secured to the divider in a back-to-back arrangement. The sterilizing elements 520a and 520b can have the same or different contour configurations. For example sterilizing element 520a can be configured to engage male luer connections and sterilizing element 520b can be configured to engage female luer connections and/or septums. Additionally, the sterilizing elements 520a and 520b can be pre-moistened with the same or different anti-pathogenic agent. According to yet another embodiment, the second sterilizing element 520b can be dry and can be used to dry the working end-site after the working end-site has been cleaned and sterilized using the first pre-moistened sterilizing element 520a. The second portion 564 containing the dry sterilizing element can be left engaged with the working end-site until the end-site is ready for use.

Figure 17:
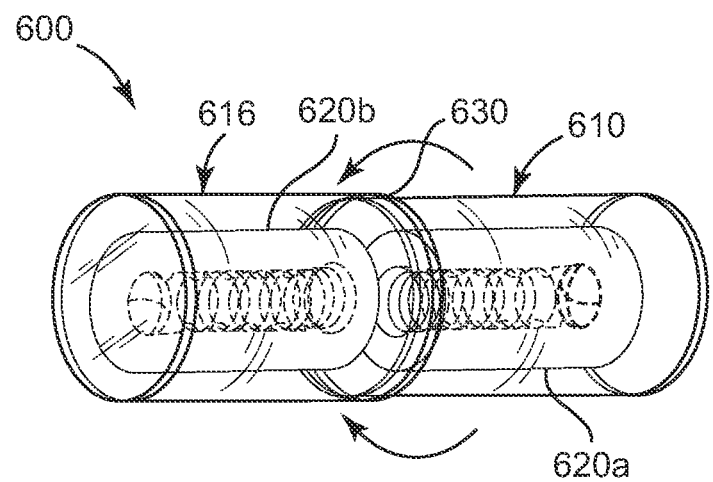
FIGS. 17 and 18 are isometric views of a combined sterilizing device according to yet another embodiment of the present invention.
Figure 18:
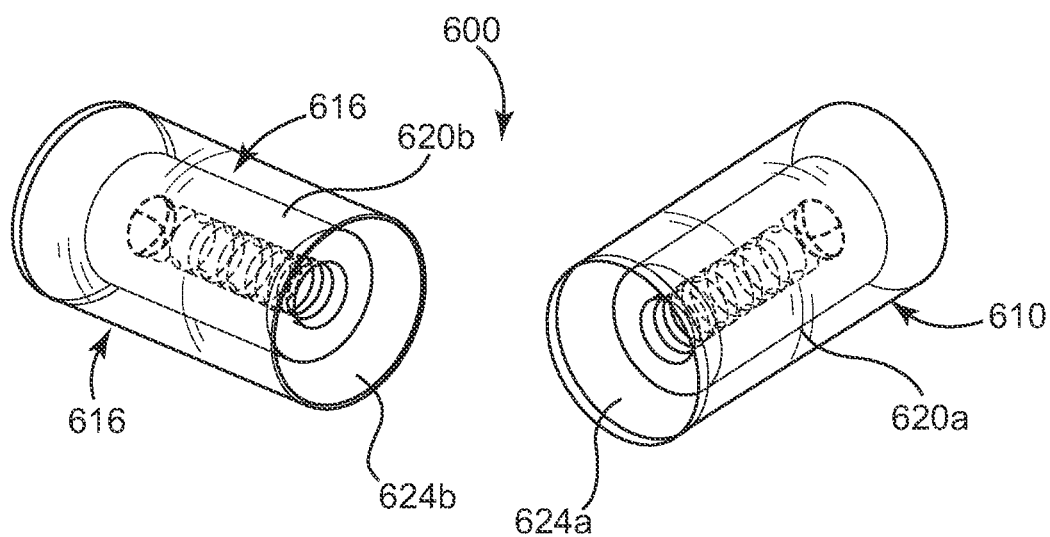

FIGS. 17 and 18 show a combined sterilizing device 600 according to yet another embodiment of the present invention. As shown in FIGS. 17 and 18, the sterilizing device 600 includes a housing 610 and a cover 616. Each of the housing 610 and the cover 616 contain a sterilizing element 620a and 620b, respectively. The sterilizing elements 620a and 620b can have any one of the configurations according to the various embodiments described above. The cover 616 is coupled to the housing 610 via a frangible seal 630, as shown in FIG. 17. The cover 616 can be separated from the housing 610 by a twisting and pulling motion to gain access to the sterilizing elements 620a and 620b through separate openings 624a and 624b located in the housing 610 and the cover 616, respectively. The housing and cover portions 610 and 616 of the device 600 can be used separately to clean and sterilize the working end-sites of one or more devices to be sterilized. According to further embodiments, the sterilizing elements 620a and 620b contained within the housing 610 and cover 616, respectively, can have the same or different configurations. Additionally, the sterilizing elements 620a and 620b can be pre-moistened with the same or different anti-pathogenic agent. For example, the sterilizing element 620a located within the housing 610 can be contoured so as to contact and engage the surfaces of male devices and can be pre-moistened with a first anti-pathogenic agent, and the sterilizing element 620b located within the cover 616 can be contoured so as to contact and engage the inner surfaces and a device having a lumen and/or septum and can be pre-moistened with the same or a second anti-pathogenic agent. According to other embodiments, the first sterilizing element 620a can be pre-moistened with an anti-pathogenic agent and is used to clean and sterilize the working end-site. The second sterilizing element 620b can be dry and used to dry the working end-site after it has been cleaned using the first sterilizing element 620a. The cover 616 including the dry sterilizing element 620b may be left engaged with the working end-site until the site is ready for use.

Figure 19:
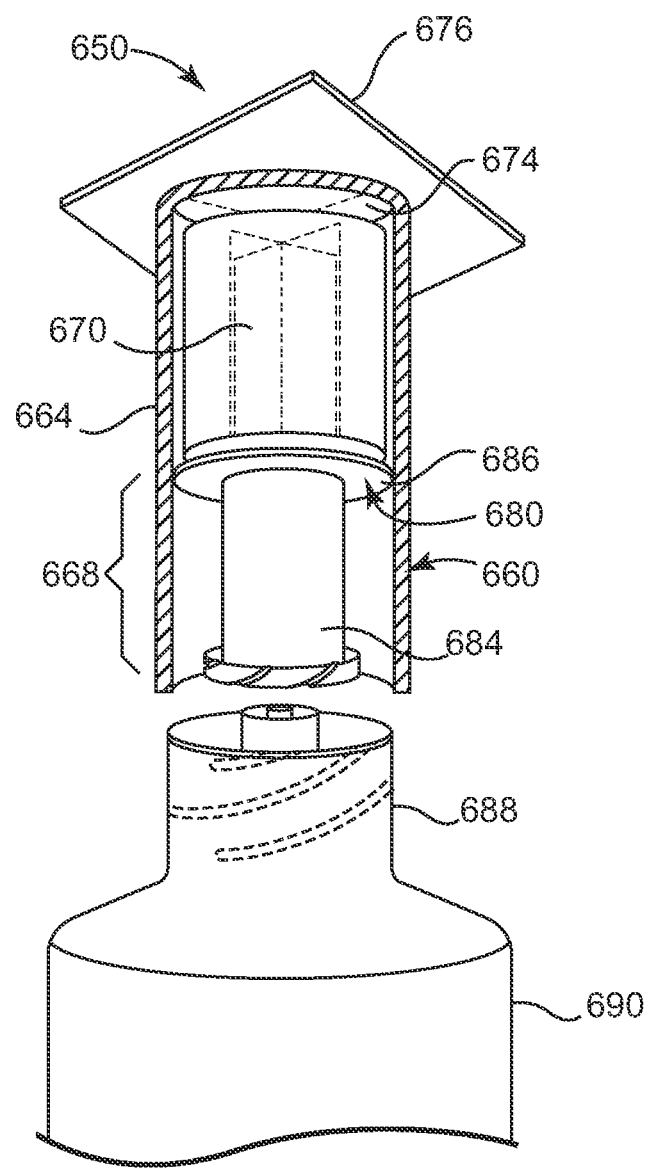
FIG. 19 is a partial cut-away view of a sterilizing device configured to be attachable to a syringe according to another embodiment of the present invention.

FIG. 19 is a partial cut-away view of a sterilizing device 650 according to another embodiment of the present invention. As shown in FIG. 19, the sterilizing device 650 includes an elongated housing 660 having an upper portion 664 and a lower portion 668. A pre-moistened sterilizing element 670, according to any one of the various embodiments as described above, is sealed within the upper portion 664 of the housing 660 by a frangible top 674. According to one embodiment, a protective cover 676, such as previously described above, can be provided over the frangible top 674. The lower portion 668 of housing 660 includes a divider or partition 680 and a female luer 684 attached to an underside 686 of the divider 680. The female luer 684 is configured such that it can be secured onto a working end 688, for example, of a male luer lock syringe 690 or slip luer style syringe. The lower portion 668 of the housing 660 covers the syringe end 688 when the female luer 684 is coupled to the syringe 690. Thus, the device 650 serves as both a sterilizing tool and as an end-cap to keep the syringe end sterile and free from debris until the syringe is ready for use. After the working end-site of the medical connector has been wiped free of debris and is sterilized using the device 650, the housing 660 and lower portion 668, including the female luer 684, can be disengaged from the male end 688 of the syringe 690, and the contents of the syringe 690 can then be injected into the working end-site of the sterilized medical connector.

Figure 20:
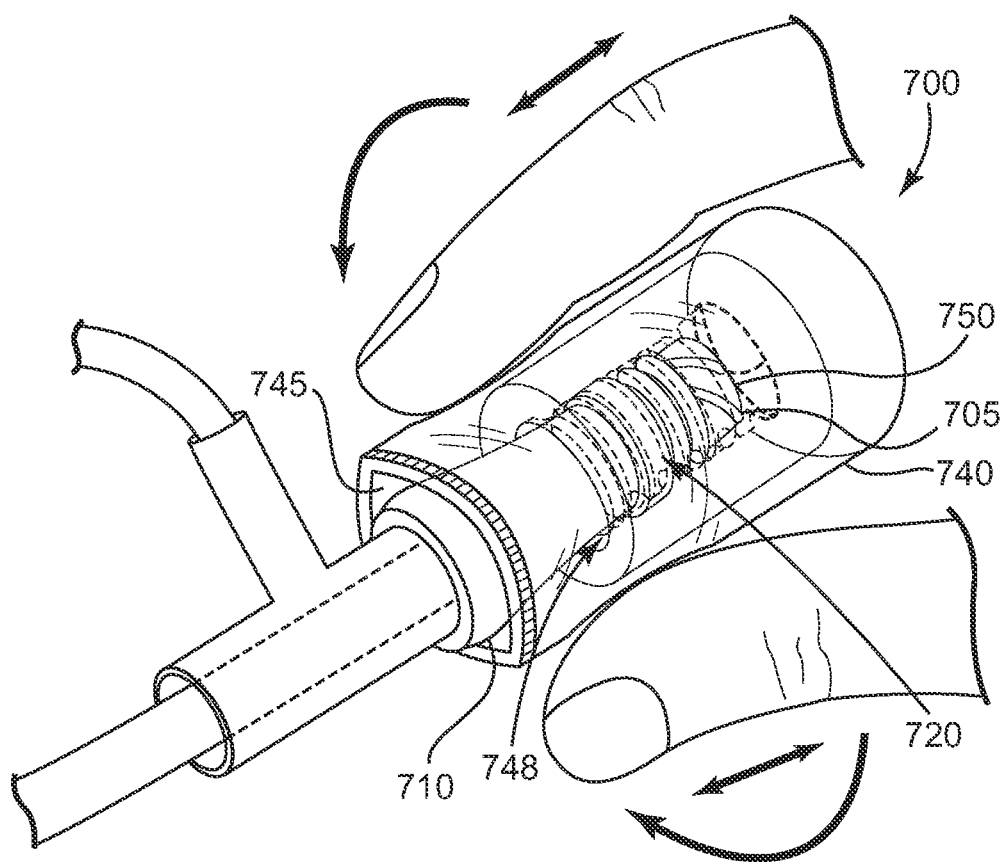
FIG. 20 is a perspective view of a sterilizing device including a sterilizing element provided in accordance with various embodiments of the present invention, in use.

FIG. 20 shows a sterilizing device 700 according to the various embodiments of the present invention, as described above, used to sterilize the working end-site 705 of a medical device 710. The sterilizing device 700 is intended for a single application and should be disposed of in the appropriate waste receptacle. The sterilizing device 700 includes a contoured sterilizing element 720 pre-moistened with an anti-pathogenic agent contained within a housing 740. In order to use the sterilizing device 700, the protective cover (if present) is first removed. Next, the housing 740 is opened to facilitate access to the sterilizing element. According to some embodiments, the housing 740 can be opened by peeling away or removing a lid secured to the top of housing. In other embodiments, the housing 740 may be opened by the application of inward pressure on the housing side walls to either break a seal formed at the top of the housing 740 or to pop off a lid. In still other embodiments, a working end-site of a device to be sterilized can be forcibly engaged through a frangible pre-scored lid or foil/laminated top to gain access to the sterilizing element 720 contained within the housing 740.

Once the housing 740 has been opened, the working end-site 705 of the device to be sterilized 710 is then inserted through the opening 745 of the sterilizing device housing 740 to access the sterilizing element 720 contained within, as shown in FIG. 20. The end-site 705 is inserted into the recessed portion 748 of the sterilizing element 720, such that the sterilizing element 720 contours to the outer threads, edges, sides, and inner lumen surfaces of the medical connector end. As shown in FIG. 20, the sterilizing element 720 includes a recessed portion 748 configured to contour to the outer surfaces and threads of the end-site and a raised base portion 750 adapted to contact and engage the distal end including the distal tip of the working end-site 705 as well as the inner lumen of the medical connector, as described above.

Debris is cleared from and an inclusive layer of ant-pathogenic agent is applied to the end surfaces of the working end-site 705 with the contoured sterilizing element 720 using a wiping and/or twisting motion for sufficient amount of time so as to achieve a specific "kill of microbes." According to some embodiments, cleaning and sterilizing the working end-site 705 includes expelling the anti-pathogenic agent onto the working end-site 705. For example, in one embodiment, the working end-site 705 is compressed into the sterilizing element 720 to expel the anti-pathogenic agent from the element 720 and onto the working end-site 705. In another exemplary embodiment, the anti-pathogenic agent can be expelled onto the working end-site 705 by squeezing the sidewalls of the housing 740 to compress the sterilizing element 720 contained therein to expel the anti-pathogenic agent onto the working end-site 705. According to one embodiment, the cleaning time is less than about 30 seconds. According to another embodiment, the cleaning time ranges from about 20 to about 30 seconds; from about 15 to about 30 seconds; or from about 10 to about 30 seconds. In some embodiments, the sterilizing device 740 may be left engaged with the working end-site 710 until ready for use.

Once the working end-site 705 has been cleaned and sterilized for the appropriate amount of time, the working end-site then can be removed from the sterilizing element 720 and the housing 740, and allowed to air dry prior to connection of another compatible device or an injection made therein with a syringe. According to one embodiment, the drying rate after the anti-pathogenic agent has been applied to the working end-site is less than about 15 seconds. In other embodiments, the drying rate is less than about 10 seconds. In still other embodiments, the drying rate is less than about 7 seconds.

In other embodiments, a second end of the sterilizing device or an additional device including a dry element may be used to wipe dry the working end-site 705 after it has been cleaned and sterilized as described above. The second end or additional drying device may be left in place engaged within the working end-site until ready for use.

Figure 21A:
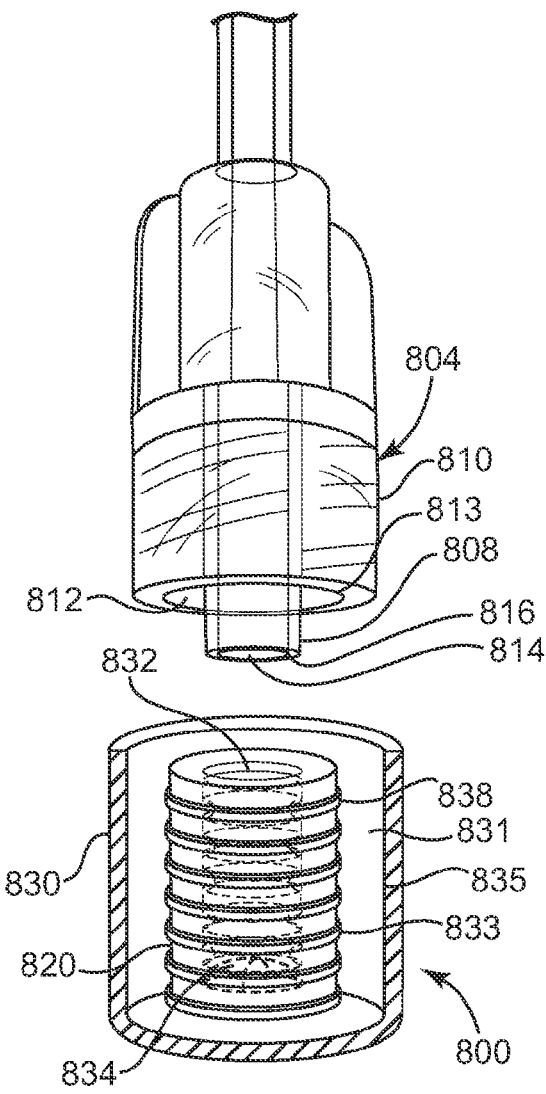
FIG. 21A is a partial cut-away view of a sterilizing device provided in accordance with various embodiments of the present invention and a male luer lock connector end.

FIG. 21A is a partial cut-away view of a sterilizing device 800 provided in accordance with various embodiments of the present invention and an exemplary connector end 804. As shown in FIG. 21A, the exemplary connector end 804 is a male luer lock connector including a male slip luer component 808 and a shroud 810 that covers and protects the slip luer component 808. An internal cavity 812 is defined between the shroud 810 and the slip luer component 808. The internal cavity 812 may include a plurality of internal threads provided on an inner wall or surface 813 of the shroud 810. The male slip luer component 808 includes a lumen 814 having an inner surface 816 and completes the fluid pathway common to male luer lock connectors.

According to various embodiments, the sterilizing device 800 includes a sterilizing element 820 contained within a housing 830. The sterilizing element 820 can have any one of the configurations according to the various embodiments described above. In one exemplary embodiment, the sterilizing element 820 includes an absorbent material pre-moistened with an anti-pathogenic agent. In certain embodiments, as shown in FIG. 21A. The housing 830 defines a cavity 831 between an outer surface 833 of the sterilizing element 820 and an inner wall 835 of the housing 830 to receive and couple with the male luer lock shroud 810. Additionally, the sterilizing element 820 includes a recessed portion 832 configured to receive and conform to the male slip luer component 808 (if present). Additionally, the sterilizing element 820 includes a raised base portion 834 configured to project into and engage an inner surface 816 of the slip luer lumen 814. Further, in certain embodiments, the outer surface 833 of the sterilizing element can be contoured to include, but not limited, ribs, threads, flanges or raised structures 838 and to contact all inner walls of the shroud 810 and to facilitate the wiping and sterilizing therein. The housing 830 can have a number of configurations, according to the various embodiments described above.

Figure 21B:
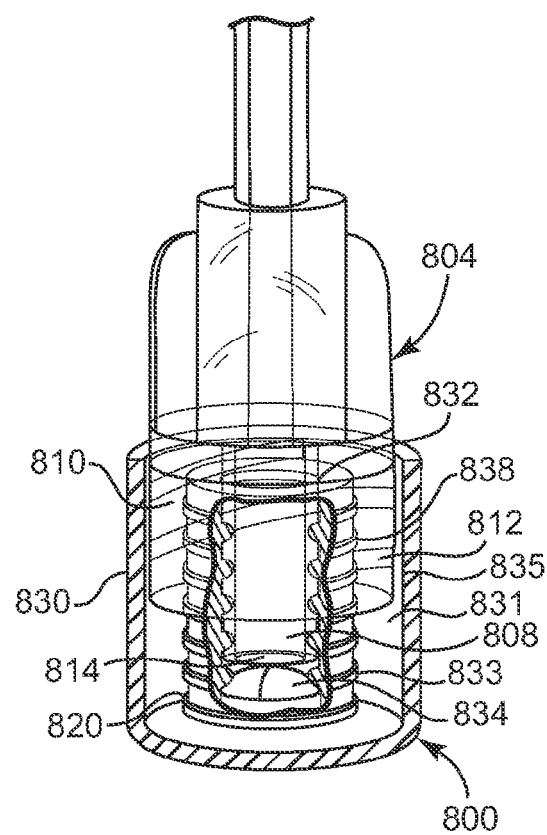
FIG. 21B is a partial cut-away view of the sterilizing device shown in FIG. 21A used to clean the male luer lock connector end.

FIG. 21B is a partial cut-away view of the sterilizing device 800 coupled with the male luer lock connector 804. In certain embodiments, as shown in FIG. 21B, the housing 830 is sized to fit over the shroud 810. The male slip luer component 808 (if present) is received and engaged in the recessed portion 832 of the sterilizing element. The sterilizing element 820, as shown in FIG. 21B, fills the internal cavity 812 defined by the shroud 810. Additionally, the shroud 810 fits sufficiently in housing cavity 831 between inner housing wall 835 and the outer wall 833 of the sterilizing element 820. The raised base portion 834 projects into and engages the inner surface 816 of the slip luer lumen 814. In some embodiments, the outer wall 833 of the sterilizing element 820 may include external surface features 838 configured to engage and contact any internal threads provided on the internal surfaces 813 of the shroud 810. Once the male luer connector 804 is engaged within the sterilizing element 820 contained within the housing 830, a wiping and/or twisting motion can be employed to wipe debris from and apply an inclusive layer of the anti-pathogenic agent to the inner and outer surfaces 812 of the male luer connector 804 including the inner surface 816 of the lumen 814. Once the male luer connector 804 has been effectively cleaned and sterilized, the sterilizing device 800 can be left on the end-site to protect its sterility until time of use and then disposed of in the appropriate waste receptacle. In certain embodiments, such as in the absence of a male connection component, the sterilizing element can be inserted into the cavity 831 defined by the shroud 810. Once the sterilizing element is engaged in the shroud, a wiping and/or twisting motion can be employed to clean and sterilize the surfaces of the medical device to be cleaned. The sterilizing device 820 can be left engaged in the shroud 810 until the device is ready for use.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A sterilizing device comprising:
    a housing comprising:
        at least one or more open end adapted to receive a working end-site of a medical device;
        one or more sidewalls having one or more outer surfaces; and
        one or more inner surfaces;
    a seal covering the at least one or more open end; and
    a sterilizing element contained and secured within the housing, the sterilizing element comprising:
        a resilient article comprising a material impregnated with an antipathogenic agent, an antipathogenic agent bonded to the resilient article or both, wherein the resilient article is a lining of the one or more inner surface of the housing, wherein the lining comprises an open recess shaped to receive the working end-site, the open recess comprising:
            an open end,
            a base portion opposite the open end, wherein the base portion comprises a projecting structural contour, and
            a sidewall extending from the base portion to the open end, wherein the sidewall comprises a plurality of projecting structural contours and a first structural contour of the plurality of projecting structural contours adjoins the base portion, wherein one or more structural contour is configured to contact a surface of the working end-site, and wherein the base portion and the plurality of structural contours comprise a single continuous resilient article.

2. The sterilizing element of claim 1, wherein the resilient article is impregnated with the antipathogenic agent and an antipathogenic agent is bonded to the resilient article.

3. The sterilizing element of claim 1, wherein the sterilizing device is configured to produce an audible popping sound when the seal is opened.

4. The sterilizing element of claim 3, wherein the seal is configured to be opened single handedly.

5. The sterilizing element of claim 1, wherein the one or more inner surfaces of the housing comprise one or more protrusions.

6. The sterilizing device of claim 5, wherein the resilient article lines the housing and one or more of the protrusions of the housing form one or more of the plurality of projecting structural contours of the resilient article.

7. The sterilizing element of claim 1, wherein the plurality of structural contours comprise a plurality of raised contouring structures and recessed contouring structures.

8. The sterilizing element of claim 7, wherein the plurality of structural contours comprise one or more of or a combination of contours selected from the group consisting of: ridges, ribs, steps, threads, and flanges.

9. The sterilizing device of claim 7, wherein one or more of the raised structural contours, one or more of the recessed structural contours or both are configured between the base portion and the open end.

10. The sterilizing element of claim 1, wherein the projecting structural contour of the base portion contacts and structurally engages an inner surface of the working end-site.

11. The sterilizing element of claim 10, wherein the projecting structural contour of the base portion comprises one or a combination of shapes selected from the group consisting of: a nipple, a nub, a bump, and a tine.

12. The sterilizing element of claim 1, wherein the sterilizing element is a dual-purpose resilient article that is structurally contoured (a) to wipe and sterilize structural contours of the end-site with the structural contours of the sterilizing element and be removed from the end-site after sterilizing the end-site, or (b) to frictionally and form-fittingly engage the structural contours of the working end-site with the structural contours of the sterilizing element and to be left on the working end-site and to be retained on the working end-site until use.

13. The sterilizing element of claim 1, wherein a portion of the base portion comprises the antipathogenic agent.

14. The sterilizing element of claim 1, wherein the first structural contour is configured to contact and to engage a surface of the working end-site.

15. The sterilizing device of claim 1, wherein one or more of the plurality of projecting structural contours is an outward projecting structural contour or an inward projecting structural contour.

16. The sterilizing element of claim 1, wherein the seal is configured to open and comprises one or more openings.

17. A sterilizing device comprising:
    a housing comprising:
        at least one open end adapted to receive a working end-site of a medical device;
        one or more sidewalls having one or more outer surfaces; and
        one or more inner surfaces;

a seal covering the at least one open end; and
a sterilizing element contained and secured within the housing, the sterilizing element comprising:
   a resilient article comprising a material impregnated with an antipathogenic agent, wherein the resilient article is a lining of the one or more inner surfaces of the housing, wherein the lining comprises an open recess that is a continuous article shaped to receive the working end-site of the medical device, the open recess comprising:
      an open end,
      a base portion opposite the open end, wherein the base portion comprises a projecting structural contour, and
      a sidewall extending from the open end to the base portion, wherein the sidewall comprises a plurality of structural contours and wherein the open recess diameter narrows from the open end to the base portion, and a first structural contour adjoins the base portion, wherein one or more of the plurality of structural contours is configured to contact and to engage a surface of the working end-site, and wherein at least a portion of the resilient article comprises the antipathogenic agent.

18. The sterilizing device of claim 17, wherein the plurality of structural contours comprise a plurality of raised contouring structures.

19. The sterilizing device of claim 17, wherein the plurality of structural contours comprise a plurality of recessed contouring structures.

20. The sterilizing device of claim 17, wherein one or more of the raised structural contours, one or more of the recessed structural contours or both are configured between the base portion and the open end.

21. The sterilizing device of claim 17, wherein one or more of the plurality of projecting structural contours is an outward projecting structural contour or an inward projecting structural contour.

22. The sterilizing device of claim 17, wherein the one or more inner surfaces of the housing comprise one or more protrusions, wherein the resilient article lines the one or more inner surfaces of the housing and one or more of the protrusions form one or more of the plurality of structural contours of the resilient article.

23. The sterilizing device of claim 17, wherein the base portion is ridged and configured to friction fit into at least one of: a septum and a lumen.

24. The sterilizing device of claim 23, wherein the base portion is configured to actuate a septum and engage a lumen.

25. The sterilizing device of claim 17, wherein one or more of the plurality of structural contours has a diameter less than an outer diameter of the end-site and wherein one or more of the plurality of structural contours is configured to engage one or more outer surfaces of the end-site to form a friction fit and to secure the sterilizing element onto the end-site.

26. The sterilizing device of claim 17, wherein one or more of the plurality of structural contours is thread-able onto the end-site.

27. A resilient contoured sterilizing element for sterilizing an end-site of a needleless connector, the resilient contoured sterilizing element comprising:
a first end and a second end; and
at least one exterior wall extending between the first end and the second end,
the first end comprising an open recess configured to receive the end-site of the needleless connector, wherein the open recess is a resilient continuous article comprising:
   an open end,
   a contoured base portion opposite the open end, wherein the base portion comprises a projecting structural contour, and
   a sidewall extending from the base portion to the open end, wherein the sidewall comprises a plurality of projecting structural contours, wherein the plurality of structural contours array from the base portion to the open end, wherein a first projecting structural contour of the plurality of structural contours adjoins the base portion, wherein one or more structural contour is configured to contact and engage a surface of the working end-site, wherein at least a portion of the sterilizing element comprises an antipathogenic agent, and wherein the contoured base portion and the plurality of structural contours comprise a single continuous resilient article.

28. The sterilizing element of claim 27, further comprising a housing containing the sterilizing element.

29. The sterilizing element of claim 28, wherein the sterilizing element is configured to be entirely removed from the housing and directly held and used by a clinician.

30. The sterilizing element of claim 28, wherein the first and second ends of the sterilizing element are coplanar with one or more openable ends of the housing.

31. The sterilizing element of claim 28, wherein the open end is coplanar with an open end of the housing.

32. The sterilizing element of claim 28, wherein one or more of the plurality of structural contours is coplanar with an open end of the housing and wherein there is one or more gaps between the plurality of structural contours that form one or more cavities with the needleless connector when the needleless connector is engaged with the open recess.

33. The sterilizing element of claim 28, wherein a circumferential gap including one or more cavities is between the housing and the sterilizing element.

34. The article of claim 28, wherein the housing comprises a sealed first end and a sealed second end, where at least one of the sealed first end and the sealed second end are openable and configured to receive the needleless connector.

35. The sterilizing element of claim 34, wherein the seal prolapses and pushes inward and down into the housing when the needleless connector is forcibly engaged through the frangible seal and wherein in together or in combination with one or more of the frangible seal, the housing, and the sterilizing element is configured to remain frictionally secured on the needleless connector until ready for use.

36. The sterilizing element of claim 28, wherein the housing is a single housing having a first end and a second end, wherein the housing comprises a single continuous open cavity from the first end to the second end and wherein at least one of the first end and the second end are openable and wherein the housing includes the sterilizing element.

37. The sterilizing element of claim 28, wherein the housing has one or more openable ends, wherein two or more housings are joined together on an end of the housing and wherein the joined housings are configured to be separated and opened to sterilize one or more end-site.

38. The sterilizing element of claim 28, wherein the housing is rectangular and wherein the housing has one or more end and one or more rectangular openings.

39. The sterilizing element of claim 28, wherein the housing is comprised of a flexible laminated package that envelops and encloses the at least one exterior wall of the sterilizing element.

40. The sterilizing element of claim 27, wherein the sterilizing element and the structural contours is a single continuous resilient article.

41. The sterilizing element of claim 27, wherein the recess comprises a continuous plurality of structures comprised of a single continuous resilient article.

42. The sterilizing element of claim 27, wherein the sterilizing element is absorbent.

43. The sterilizing element of claim 27, wherein one or more of the plurality of structural contours is coplanar with at least one of: the first end and the second end.

44. The sterilizing element of claim 27, wherein one or more of the plurality of structural contours is coplanar with the open recess and wherein there is one or more gaps between the plurality of structural contours that form one or more cavities with the needleless connector when the needleless connector is engaged with the open recess.

45. The sterilizing element of claim 27, wherein the exterior wall includes a plurality of structural contours, wherein one or more of the plurality of structural contours is coplanar with the open end and wherein there is one or more gap between the plurality of structural contours that form one or more cavities with a housing when the needleless connector is engaged with the open recess.

46. The sterilizing element of claim 27, wherein the open recess extends beyond the threading of the needleless connector when the needleless connector is engaged with the open recess.

47. The sterilizing element of claim 27, wherein the open recess has one or more gap in between one or more of the plurality of structural contours that form one or more cavities with the needleless connector when the needleless connector is engaged with the open recess.

48. The sterilizing element of claim 27, wherein the resilient article is contained within a housing comprising one or more ends that are openable.

49. The sterilizing element of claim 27, wherein the sterilizing element cleans the end-site using at least one of: a push-pull motion, a wiping motion, a twisting motion, a dabbing motion and a screwing motion.

50. The sterilizing element of claim 27, wherein the resilient article comprises particulate-free material to remove debris from the end-site.

51. The sterilizing element of claim 50, wherein removing debris includes removing at least one of: microbes and an antipathogenic residue.

52. The sterilizing element of claim 27, wherein a portion of the resilient article is comprised of a semi-rigid resilient material.

53. The sterilizing element of claim 27, wherein the structural contours apply a inclusive layer of antipathogenic agent to one or more surfaces of the end-site.

54. The sterilizing element of claim 27, wherein the resilient article incorporates a ratio of antipathogenic agent to the amount of resilient material and expels a measured controlled amount onto the end-site to promote a dry time less than 7 seconds.

55. The sterilizing element of claim 27, wherein the resilient article is sufficiently rigid to prevent over-compression and to expel a measured controlled amount onto the end-site to promote a dry time less than 7 seconds.

56. The sterilizing element of claim 27, wherein the rigid article prevents an uncontrolled release of antipathogenic agent and to expel a measured controlled amount onto the end-site to promote a dry time less than 7 seconds.

57. The sterilizing element of claim 27, wherein the resilient article is semi-ridged and the structural contours apply a layer of antipathogenic to the needleless connector to promote a sterilization of the needleless connector of less than 11 seconds.

58. The sterilizing element of claim 27, wherein squeezing or pinching the exterior walls of the resilient article expels antipathogenic agent.

59. The sterilizing element of claim 27, wherein one or more ends of the sterilizing element is configured to perform at least one or a combination of: sterilizing, drying, wiping and cleaning.

60. A resilient contoured sterilizing element for sterilizing an end-site of a needleless connector, the resilient contoured sterilizing element comprising:
a first end and a second end; and
at least one exterior wall extending between the first end and the second end,
the first end comprising an open recess configured to receive the end-site of the needleless connector, wherein the open recess is a resilient continuous article comprising:
an open end;
a contoured base portion opposite the open end; and
a sidewall extending from the open end to the base portion, wherein the sidewall comprises a plurality of projecting structural contours, wherein the diameter of the open recess narrows from the open end to the base portion, wherein a first structural contour of the plurality of projecting structural contours adjoins the contoured base portion, wherein the plurality of projecting structural contours progress from the base portion toward the open end, wherein one or more of the contours is configured to contact and to engage a surface of the working end-site, wherein at least a portion of sterilizing element comprises the antipathogenic agent, and wherein the contoured base portion and projecting structural contours comprise a single resilient continuous article.

61. The sterilizing element of claim 60, further comprising a housing containing the resilient contoured sterilizing element.

62. The sterilizing element of claim 61, wherein the sterilizing element is configured to be entirely removed from the housing and directly held and used by a clinician.

63. The sterilizing element of claim 61, wherein the first and second ends of the sterilizing element is coplanar with one or more openable ends of the housing.

64. The sterilizing element of claim 61, wherein the open end is coplanar with an open end of the housing.

65. The sterilizing element of claim 61, wherein one or more of the plurality of structural contours is coplanar with an open end of the housing.

66. The sterilizing element of claim 61, wherein a circumferential gap is between the housing and the sterilizing element.

67. The sterilizing element of claim 61, wherein the housing is a single housing having a first end and a second end, wherein the housing comprises a single continuous cavity from the first end to the second end and wherein at least one of the first end and the second end are openable.

68. The sterilizing element of claim 61, wherein the housing has one or more openable ends, wherein two or more housings are joined together at an end of the housing and wherein the joined housings are configured to be separated and opened to sterilize one or more end site.

69. The sterilizing element of claim 61, wherein the housing has at least one open end that is oval shape.

70. The sterilizing element of claim 61, wherein inner surfaces of the housing comprise one or more protrusions including at least one or a combination of: ribs, points and indentations to secure the resilient article.

71. The sterilizing element of claim 61, wherein at least one or a combination of: ultrasonic welding, adhesives, outward radial expansion and fictional engagement are used to secure to the resilient article to the housing.

72. The sterilizing element of claim 61, wherein the housing comprises one or more labels and wherein one or more labels signify a status of the end-site.

73. The sterilizing element of claim 60, wherein the base portion is ridged and configured to friction fit into at least one of: a septum and a lumen.

74. The sterilizing element of claim 60, wherein the base portion is sufficiently ridged to actuate a septum, engage a lumen or both.

75. The sterilizing element of claim 60, wherein one or more of the plurality of structural contours is coplanar with at least one of: the first end and the second end.

76. The sterilizing element of claim 60, wherein one or more of the plurality of structural contours is coplanar with the sidewall.

77. The sterilizing element of claim 60, wherein the exterior wall comprised of one or more of the plurality of structural contours and where one or more contour is coplanar with the at least one or more of the first end and the second end on the exterior wall.

78. The sterilizing element of claim 60, wherein the open recess extends past threading of the needleless connector.

79. The sterilizing element of claim 60, wherein the open recess has one or more gaps in between one or more of the plurality of structural contour.

80. The sterilizing element of claim 60, wherein the open recess includes one or more engaging structural contour on the sidewall.

81. The sterilizing element of claim 60, wherein the base portion comprises one or more engaging structural contours.

82. The sterilizing element of claim 60, wherein the resilient article is contained within a housing comprising one or more ends that are openable.

83. The sterilizing element of claim 60, wherein the antipathogenic agent comprises at least one of: a liquid antipathogenic agent and a dry antipathogenic agent.

* * * * *

UNITED STATES PATENT AND TRADEMARK OFFICE
CERTIFICATE OF CORRECTION

PATENT NO. : 9,561,298 B2  
APPLICATION NO. : 13/592008  
DATED : February 7, 2017  
INVENTOR(S) : Michael J. Ferlic, Mason J. Ferlic and Nicholas R. Powley Page 1 of 1

It is certified that error appears in the above-identified patent and that said Letters Patent is hereby corrected as shown below:

In the Specification

Column 6, Line 39: replace "semi-ridged" with -- semi-rigid --.

In the Claims

Claim 23, second line: replace "ridged" with -- rigid --.

Claim 57, second line: replace "semi-ridged" with -- semi-rigid --.

Claim 73, second line: replace "ridged" with -- rigid --.

Claim 74, second line: replace "ridged" with -- rigid --.

Signed and Sealed this  
Twelfth Day of February, 2019

Andrei Iancu  
*Director of the United States Patent and Trademark Office*